(12) United States Patent
Li et al.

(10) Patent No.: US 10,513,512 B2
(45) Date of Patent: Dec. 24, 2019

(54) FLAVANONE DERIVATIVES, AND PREPARATION METHOD AND USE THEREOF

(71) Applicant: Xuanwu Hospital of Capital Medical University, Beijing (CN)

(72) Inventors: Lin Li, Beijing (CN); Hongshun Gu, Beijing (CN); Lan Zhang, Beijing (CN); Xi Chen, Beijing (CN); Linlin Yin, Beijing (CN); Ruyi Zhang, Beijing (CN); Cuicui Yang, Beijing (CN)

(73) Assignee: Xuanwu Hospital of Capital Medical University, Beijing (CN)

( * ) Notice: Subject to any disclaimer, the term of this patent is extended or adjusted under 35 U.S.C. 154(b) by 0 days.

(21) Appl. No.: 16/071,472

(22) PCT Filed: Jan. 11, 2017

(86) PCT No.: PCT/CN2017/070877
§ 371 (c)(1),
(2) Date: Jul. 19, 2018

(87) PCT Pub. No.: WO2017/124949
PCT Pub. Date: Jul. 27, 2017

(65) Prior Publication Data
US 2019/0031644 A1    Jan. 31, 2019

(30) Foreign Application Priority Data

Jan. 19, 2016 (CN) .......................... 2016 1 0032327

(51) Int. Cl.
| | |
|---|---|
| *C07D 405/12* | (2006.01) |
| *C07D 311/32* | (2006.01) |
| *C07D 413/04* | (2006.01) |
| *A61P 25/28* | (2006.01) |
| *A61P 25/22* | (2006.01) |
| *A61P 25/24* | (2006.01) |
| *A61P 25/16* | (2006.01) |
| *A61K 31/353* | (2006.01) |
| *A61K 31/454* | (2006.01) |
| *A61K 31/496* | (2006.01) |
| *A61P 25/18* | (2006.01) |
| *C07D 413/14* | (2006.01) |

(52) U.S. Cl.
CPC .......... *C07D 405/12* (2013.01); *A61K 31/353* (2013.01); *A61K 31/454* (2013.01); *A61K 31/496* (2013.01); *A61P 25/16* (2018.01); *A61P 25/18* (2018.01); *A61P 25/22* (2018.01); *A61P 25/24* (2018.01); *A61P 25/28* (2018.01); *C07D 311/32* (2013.01); *C07D 413/04* (2013.01); *C07D 413/14* (2013.01)

(58) Field of Classification Search
CPC .. C07D 405/12; C07D 405/02; C07D 311/32; C07D 413/04; A61P 25/28; A61P 25/22; A61P 25/18; A61P 25/24; A61P 25/16; A61K 31/353; A61K 31/454; A61K 31/496

See application file for complete search history.

(56) References Cited

U.S. PATENT DOCUMENTS

| | | | |
|---|---|---|---|
| 8,008,344 B2 | 8/2011 | Huang et al. | |
| 2009/0076130 A1 | 3/2009 | Huang et al. | |

FOREIGN PATENT DOCUMENTS

| | | |
|---|---|---|
| CN | 103435601 A | 12/2013 |
| CN | 103450174 A | 12/2013 |
| CN | 103694233 A | 4/2014 |
| CN | 104059046 A | 9/2014 |

OTHER PUBLICATIONS

Xiao et al., 80 Eur. J. Med. Chem. 92-100 (2014) (CAS Abstract) (Year: 2014).*
International Search Report and Written Opinion for PCT/CN2017/070877, dated Jan. 19, 2018.
International Preliminary Report of Patentability for PCT/CN2017/070877, dated Jul. 24, 2018.
Gu et al., Synthesis and biological evaluation of novel flavanone derivatives as potential antipsychotic agents. Chem Biol Drug Des. Mar. 2017;89(3):353-364. doi: 10.1111/cbdd.12843. Epub Sep. 26, 2016.

(Continued)

*Primary Examiner* — Timothy R Rozof
(74) *Attorney, Agent, or Firm* — Wolf, Breenfield & Sacks, P.C.

(57) ABSTRACT

The invention relates to flavanone derivatives, and preparation method and use thereof, particularly relates to a compound of Formula I or a pharmaceutically acceptable salt thereof, a pharmaceutical composition comprising the same, a preparation method thereof, and use thereof for preventing or treating a mental disorder or a nervous system disease. The compound of the invention exerts significant activity of inhibiting microglial activation and neuroinflammation, can antagonize dopamine D2 receptor, improve the ethological change in multiple animal models for mental disorders, effectively inhibit neuroinflammation and demyelination, and can be used to prevent or treat a mental disorder and a nervous system disease.

Formula I

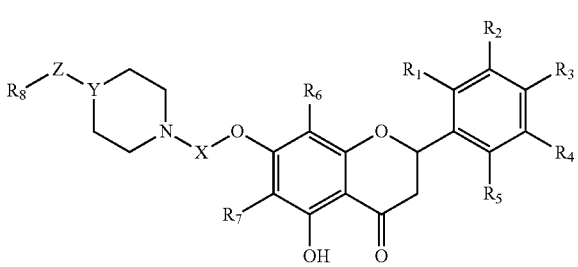

22 Claims, 9 Drawing Sheets

(56) References Cited

OTHER PUBLICATIONS

Xiao et al., Design, synthesis, and evaluation of novel fluoroquinolone-flavonoid hybrids as potent antibiotics against drug-resistant microorganisms. Eur J Med Chem. Jun. 10, 2014;80:92-100. doi: 10.1016/j.ejmech.2014.04.037. Epub Apr. 13, 2014.
Office Action for CN App. No. 201610032327.6 dated Feb. 19, 2019.
Chen, Design, Synthesis and Biological Evaluation of the Novel Multireceptor Antipsychotics. Dissertation. Huazhong University of Science and Technology. Apr. 2012. Abstract and excerpts. 14 pages.
Zhang, Study on the synthesis of Natural flavors. Dissertation. Kunming University of Science and Technology. 2014. Abstract and excerpts. 9 pages.
CN 201610032327.6, dated Feb. 19, 2019, Office Action.

* cited by examiner

FLAVANONE DERIVATIVES, AND PREPARATION METHOD AND USE THEREOF

RELATED APPLICATIONS

The present application is a national stage filing under 35 U.S.C. § 371 of International PCT Application No. PCT/CN2017/070877, filed Jan. 11, 2017. Foreign priority benefits are claimed under 35 U.S.C. § 119(a)-(d) or 35 U.S.C. § 365(b) of the People's Republic of China application number 201610032327.6, filed Jan. 19, 2016. The entire contents of each of these applications is incorporated herein by reference.

TECHNICAL FIELD

The present invention relates to the field of medicine, particularly, relates to flavanone derivatives, and preparation method and use thereof.

BACKGROUND ART

Mental disorders refer to varying degrees of disorders in mental activities including cognition, emotion, behavior and volition caused by brain dysfunction. Common mental disorders include schizophrenia, depression, manic depressive disorder (bipolar disorder), anxiety disorder, phobia, obsessive-compulsive disorder, stress-related disorder, mental disorder associated with organic lesion, etc. Statistically, mental disorders account for more than 15% of the global burden of disease. Mental diseases rank first, with a percentage of 20%, in the total burden of disease in China. It is reported that the incidence of mental diseases in China is as high as 17.5%, wherein severe mental disorders is up to 1%.

Monoamine and receptors thereof are one of the most widely studied neurotransmitters and receptors on pathogenesis in psychiatry research. The pathogenesis of schizophrenia mainly include dopamine (DA) hyperactivity hypothesis, and hypothesis concerning the neural pathway blockage of 5-hydroxytryptamine (5-HT) and norepinephrine (NE). Studies show that positive symptoms (such as hallucination, delusion, etc.) in the schizophrenics may be associated with DA hyperfunction in subcortical limbic system. Antipsychotic drugs, which exert a pharmacological action by blocking Dopamine D2 Receptor (DRD2), can effectively control positive symptoms of schizophrenia.

Glutamate and aspartate are the most common excitatory neurotransmitters in central nervous system. Studies suggest that abnormal glutamatergic transmission is involved in schizophrenia and other mental disorders. N-methyl-D-aspartic acid (NMDA) receptor antagonists can induce schizophrenia-like effects; and substances, which enhance NMDA receptor function, can improve symptoms and cognitive functions in the schizophrenics.

More and more evidences have shown that inflammation and immune dysfunction may be closely associated with the development and progression of schizophrenia, depression, and other mental disorders. In the brains of patients with schizophrenia and patients at high risk for schizophrenia, immune cells (microglial cells) are more active, indicating that neuroinflammatory response is an important factor in schizophrenia, and has become a new potential target for the treatment and prevention of schizophrenia. In addition, it is shown that, in human autopsy studies and special imaging techniques, as well as studies on animal depression models, depression may occur when microglial cells change and fail to modulate brain function and behavioral progress any more. Long-term exposure to chronic, unpredictable psychological stress can also lead to changes in the shape and function of microglial cells, and such a stress is also one of the most important causes for depression in human.

Plenty of studies indicate that microglial activation and neuroinflammation are the important pathogenesis for nervous system diseases such as neurodegenerative disease (e.g. Alzheimer's disease, Parkinson's disease), cerebrovascular disease, brain trauma, spinal cord injury, demyelinating disease, multiple sclerosis, and encephalomyelitis.

White matter, which is an important component of central nervous system, is also the place where nerve fibers accumulate. Damage of myelin sheath in central nerve cells can result in pathological changes in white matter. In patients with schizophrenia, depression and other mental disorders, as well as patients with cerebrovascular disease, diabetic neuropathy, etc., nerve fibers in white matter are abnormal, such as changes in myelin sheath, and disordered axons; and demyelinating diseases such as multiple sclerosis may have the symptoms of mental disorder. These results indicate that pathological changes in white matter are closely associated with the pathogenesis of mental disorders and some nervous system diseases.

At present, antipsychotic drugs applied in clinic can be divided into two classes: one is the first-generation antipsychotic drugs that can block dopamine receptors, known as "classical" antipsychotic drugs (such as haloperidol, etc.). Although they can effectively control the positive symptoms of schizophrenia, they have little therapeutic effect on cognitive disorder. The other one is the drugs that act on both dopamine receptor and other receptors (such as serotonin receptor, norepinephrine receptor), known as "non-classical" antipsychotic drugs (such as ziprasidone, risperidone, etc.). Although these drugs have certain therapeutic effects both on the positive symptoms and negative symptoms of schizophrenia, similarly, they have litter therapeutic effect on cognitive disorder.

To sum up, there are still no antipsychotic drugs that can improve cognitive disorder. In addition, there are not sufficient studies on these drugs that can simultaneously act on multiple targets involved in the complex pathogenesis of a mental disorder and a neurological disease, such as dopaminergic system, glutamatergic system, microglial cells and white matter.

Therefore, it is of important significance in clinical treatment to develop drugs against mental disorders and neurological diseases, which act on multiple targets.

CONTENTS OF INVENTION

The inventor of the present invention obtains a class of novel compounds through modification of flavonones. The compounds can simultaneously act on multiple targets, such as dopaminergic system, glutamatergic system, microglial cells or brain white matter, effectively improve cognitive function, and can be used to prevent or treating a mental disorder or a nervous system disease. The invention is accomplished based on the above findings.

Based on the above findings, the object of the invention resides in at least one of the following items: 1. providing a class of novel flavanone derivative or a pharmaceutically acceptable salt thereof, preparation method therefor, and a pharmaceutical composition comprising the derivative or the pharmaceutically acceptable salt thereof; 2. providing use of the flavanone derivative or the pharmaceutically acceptable or the pharmaceutical composition thereof in the manufacture of a medicament for preventing or treating a mental disorder or a nervous system disease; 3. providing a method for preventing or treating a mental disorder or a nervous system disease, comprising administering to a patient in need thereof an effective amount of the flavanone derivative or the pharmaceutically acceptable salt or the pharmaceutical composition thereof; 4. the flavanone derivative or the pharmaceutically acceptable salt or the pharmaceutical composition thereof, for use in the prevention or treatment of a mental disorder or a nervous system disease.

More particularly, in the first aspect, the invention provides a compound of Formula (I) or a pharmaceutically acceptable salt thereof, Formula (I)

$R_1$, $R_2$, $R_3$, $R_4$, $R_5$, $R_6$, $R_7$ and $R_8$ are independently selected from the group consisting of hydrogen, halogen (e.g. fluorine or chlorine), cyano, hydroxyl, amino, $C_{1-6}$alkyl (e.g. methyl), $C_{1-6}$alkoxy (e.g. methoxy), $C_{1-6}$alkylamino and aryl, optionally, wherein the $C_{1-6}$alkyl, $C_{1-6}$alkoxy, $C_{1-6}$alkylamino and aryl are independently substituted with one or more substituents selected from the group consisting of halogen (e.g. fluorine or chlorine), amino and hydroxyl;

X is a saturated or partially saturated alkylene containing 2-6 carbon atoms, optionally, wherein the alkylene is substituted with a substituent selected from hydroxyl and methyl;

Y is N or C(R), wherein R is selected from the group consisting of hydrogen, hydroxyl, amino, and $C_{1-6}$alkyl;

Z is aryl or heteroaryl.

In some preferred embodiments of the invention, $R_1$, $R_2$, $R_4$, $R_5$, $R_6$ and $R_7$ are independently selected from the group consisting of hydrogen, halogen (e.g. fluorine or chlorine), cyano, hydroxyl, amino, $C_{1-6}$alkyl (e.g. methyl), $C_{1-6}$alkoxy (e.g. methoxy), $C_{1-6}$alkylamino and 6-20-membered aryl (e.g. 6-10 membered aryl, such as phenyl or naphthyl); the other atoms and substituents have the same meanings as defined in the first aspect of the invention.

In some preferred embodiments of the invention, $R_1$, $R_2$, $R_4$, $R_5$, $R_6$ and $R_7$ are independently selected from the group consisting of hydrogen, halogen (e.g. fluorine or chlorine), cyano, hydroxyl, amino and $C_{1-2}$alkyl (e.g. methyl); the other atoms and substituents have the same meanings as defined in the first aspect of the invention.

In some preferred embodiments of the invention, $R_1$, $R_2$, $R_4$, $R_5$, $R_6$ and $R_7$ are independently selected from the group consisting of hydrogen, halogen (e.g. fluorine or chlorine), cyano, hydroxyl, amino and $C_{1-2}$alkyl (e.g. methyl); the other atoms and substituents have the same meanings as defined in the first aspect of the invention.

In some preferred embodiments of the invention, $R_1$, $R_2$, $R_4$, $R_5$, $R_6$ and $R_7$ are hydrogen; the other atoms and substituents have the same meanings as defined in the first aspect of the invention.

In some preferred embodiments of the invention, $R_3$ and $R_8$ are independently selected from the group consisting of hydrogen, halogen (e.g. fluorine or chlorine), $C_{1-6}$alkyl (e.g. methyl) and $C_{1-6}$alkoxy (e.g. methoxy), optionally, wherein the $C_{1-6}$alkyl and $C_{1-6}$alkoxy are independently substituted with one or more substituents selected from the group consisting of halogen, amino and hydroxyl;

the other atoms and substituents have the same meanings as defined in the first aspect of the invention.

In some preferred embodiments of the invention, $R_3$ is selected from the group consisting of hydrogen, halogen (e.g. fluorine or chlorine), $C_{1-4}$alkyl (e.g. methyl) and $C_{1-4}$alkoxy (e.g. methoxy), optionally, wherein the $C_{1-4}$alkyl and $C_{1-4}$alkoxy are independently substituted with one or more substituents selected from the group consisting of halogen, amino and hydroxyl;

the other atoms and substituents have the same meanings as defined in the first aspect of the invention.

In some preferred embodiments of the invention, $R_3$ is selected from the group consisting of hydrogen, halogen (e.g. fluorine or chlorine), $C_{1-2}$alkyl (e.g. methyl) and $C_{1-2}$alkoxy (e.g. methoxy);

the other atoms and substituents have the same meanings as defined in the first aspect of the invention.

In some preferred embodiments of the invention, $R_3$ is selected from the group consisting of halogen (e.g. fluorine or chlorine), $C_{1-2}$alkyl (e.g. methyl) and $C_{1-2}$alkoxy (e.g. methoxy);

the other atoms and substituents have the same meanings as defined in the first aspect of the invention.

In some preferred embodiments of the invention, $R_3$ is selected from the group consisting of fluorine, methyl and methoxy;

the other atoms and substituents have the same meanings as defined in the first aspect of the invention.

In some preferred embodiments of the invention, $R_8$ is selected from the group consisting of hydrogen, halogen (e.g. fluorine or chlorine), $C_{1-2}$alkyl (e.g. methyl) and $C_{1-2}$alkoxy (e.g. methoxy);

the other atoms and substituents have the same meanings as defined in the first aspect of the invention.

In some preferred embodiments of the invention, $R_8$ is selected from the group consisting of halogen (e.g. fluorine or chlorine), $C_{1-2}$alkyl (e.g. methyl) and $C_{1-2}$alkoxy (e.g. methoxy);

the other atoms and substituents have the same meanings as defined in the first aspect of the invention.

In some preferred embodiments of the invention, $R_8$ is selected from fluorine and methoxy;

the other atoms and substituents have the same meanings as defined in the first aspect of the invention.

In some preferred embodiments of the invention, X is $C_{2-6}$alkylene (e.g. $C_{2-4}$alkylene, for example, 1,2-ethylene, 1,3-propylene or 1,4-butylene), optionally, the $C_{2-6}$alkylene is substituent with a substituent selected from hydroxyl and methyl;

the other atoms and substituents have the same meanings as defined in the first aspect of the invention.

In some preferred embodiments of the invention, X is 1,3-propylene or 1,4-butylene;

the other atoms and substituents have the same meanings as defined in the first aspect of the invention.

In some preferred embodiments of the invention, Y is N or C(R), wherein R is selected from the group consisting of hydrogen, hydroxyl and methyl;

the other atoms and substituents have the same meanings as defined in the first aspect of the invention.

In some preferred embodiments of the invention, Y is N or CH;

the other atoms and substituents have the same meanings as defined in the first aspect of the invention.

In some preferred embodiments of the invention, Z is aryl or heteroaryl containing 5-20 carbon atoms (e.g. 5-15 carbon atoms, such as 5-10 carbon atoms);

the other atoms and substituents have the same meanings as defined in the first aspect of the invention.

In some preferred embodiments of the invention, Z is aryl containing 6-20 carbon atoms (e.g. 6-15 carbon atoms, such as 6-10 carbon atoms) or 5-20-membered heteroaryl (e.g. 5-15-membered heteroaryl, such as 5-10-membered heteroaryl);

the other atoms and substituents have the same meanings as defined in the first aspect of the invention.

In some preferred embodiments of the invention, Z is selected from the group consisting of phenyl, naphthyl, pyrrolyl, furyl, thienyl, imidazolyl, pyrazolyl, oxazolyl, isoxazolyl, thiazolyl, isothiazolyl, triazolyl, pyridyl, pyranyl, pyrimidinyl, pyrazinyl, pyridazinyl, triazinyl, indolyl, benzofuryl, benzothienyl, benzoimidazolyl, benzopyrazolyl, benzoxazolyl, benzisoxazolyl, benzothiazolyl, benzoisothiazolyl, benzotriazolyl, quinolyl, benzopyranyl, benzopyrimidinyl, quinoxalinyl, benzopyridazinyl, benzotriazinyl and purinyl;

the other atoms and substituents have the same meanings as defined in the first aspect of the invention.

In some preferred embodiments of the invention, Z is selected from phenyl and benzisoxazolyl.

In some preferred embodiments of the invention, the compound is selected from the group consisting of:

5-hydroxy-2-(4-methoxyphenyl)-7-(4-(4-(2-methoxyphenyl)-piperazin-1-yl)-butoxy)-chroman-4-one;

5-hydroxy-2-(4-methylphenyl)-7-(4-(4-(2-methoxyphenyl)-piperazin-1-yl)-butoxy)-chroman-4-one;

5-hydroxy-2-(4-fluorophenyl)-7-(4-(4-(2-methoxyphenyl)-piperazin-1-yl)-butoxy)-chroman-4-one;

5-hydroxy-2-(4-methoxyphenyl)-7-(4-(4-(2-methoxyphenyl)-piperazin-1-yl)-propoxy)-chroman-4-one;

5-hydroxy-2-(4-methoxyphenyl)-7-(4-(4-(6-fluoro-benzo[d]isoxazol-3-yl)-piperidin-1-yl)-butoxy)-chroman-4-one;

5-hydroxy-2-(4-methoxyphenyl)-7-(4-(4-(6-fluoro-benzo[d]isoxazol-3-yl)-piperidin-1-yl)-propoxy)-chroman-4-one; and 5-hydroxy-2-(4-fluorophenyl)-7-(4-(4-(6-fluoro-benzo[d]isoxazol-3-yl)-piperidin-1-yl)-butoxy)-chroman-4-one.

In the second aspect, the invention provides a method for preparing the compound or the pharmaceutically acceptable salt thereof according to the first aspect of the invention, characterized in that the flavanone moiety at the right side of the X group is synthesized first, and then is linked to a piperazinyl or piperidyl group substituted with a substituted phenyl or 1,2-benzisoxazolyl, via a carbon chain containing 2-6 carbon atoms, to produce the compound, wherein the atoms and substituents have the same meanings as defined in the first aspect of the invention.

In an embodiment of the invention, the method comprises the following steps:

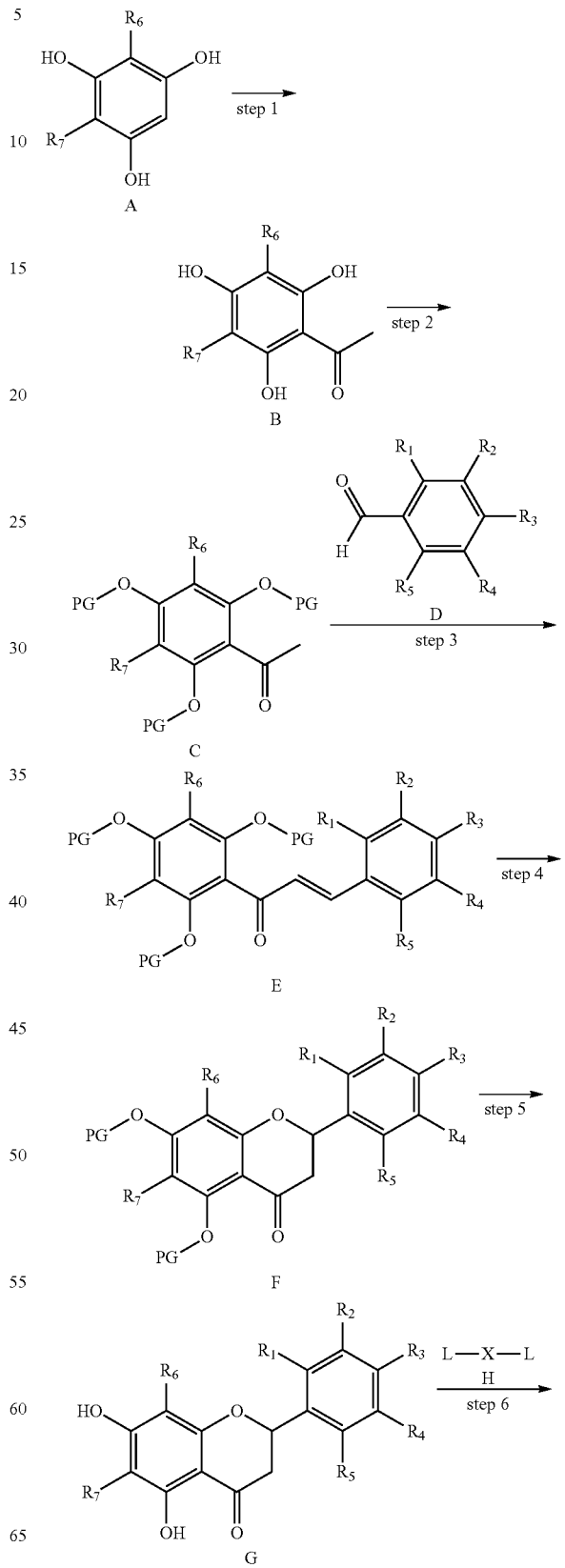

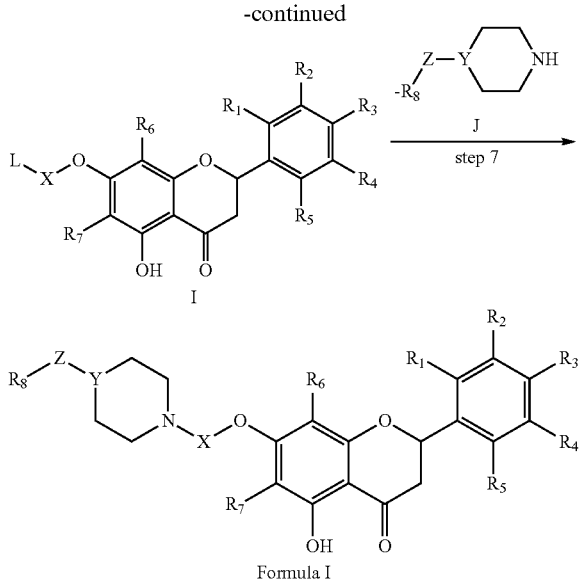

Formula I

1) Compound A and acetyl chloride are subjected to acylation reaction to produce Compound B;

2) Protective groups for the hydroxyl groups of Compound B are introduced to produce Compound C;

3) Compound C and Compound D are subjected to aldol condensation reaction to produce Compound E;

4) Compound E is subjected to ring-closure reaction to produce Compound F;

5) Compound F is deprotected to produce Compound G;

6) Compound G and Compound H are subjected to nucleophilic substitution to produce Compound I; and, 7) Compound I and Compound J are subjected to nucleophilic substitution to produce Compound of Formula I;

wherein, PG represents a hydroxyl protecting group, e.g. MOM, TMS or TBS, etc.; L represents a leaving group of the nucleophilic substitution reaction, e.g. halogen, —OTs, —OCOR (R represents alkyl), etc.;

the other atoms or substituents have the same meanings as defined in the first aspect of the invention.

In the third aspect, the invention provides a pharmaceutical composition, comprising the compound of Formula I or the pharmaceutically acceptable salt thereof according to the first aspect of the invention, and optionally one or more pharmaceutically acceptable adjuvants (e.g. carriers and/or excipients, etc.).

In the embodiments of the invention, the adjuvant refers to a substance other than an active ingredient, which has been reasonably evaluated for safety, and is comprised in a pharmaceutical formulation; for example, a carrier or an excipient. The carrier described herein includes, but is not limited to, an ion exchanger, aluminum oxide, aluminum stearate, lecithin, serum protein such as human serum albumin; a buffer substance such as phosphate, glycerol, sorbic acid, potassium sorbate, a partial glyceride mixture of saturated plant fatty acid, water, a salt or an electrolyte, such as protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethylcellulose sodium, polyacrylic ester, beewax, and lanocerin. The excipient used herein refers to an additive other than a main drug in a pharmaceutical formulation, which is stable in property, is not incompatible with the main drug, does not result in side effects, does not affect the therapeutic effect, is not easily deformed, cracked, moldy, and worm-damaged at room temperature, is not harmful to human body, has no physiological action, does not react with the main drug chemically or physically, does not influence the determination of the content of the main drug, and so on. The excipient can be, for example, a binding agent, a filler, a disintegrating agent, and a lubricant in a tablet; alcohol, vinegar, medicine juice, and the like in a pill of traditional Chinese medicine; the base material in a semi-solid formulation such as ointment and cream; a preservative, an antioxidant, a flavoring agents, an aromatic, a co-solvent, an emulsifier, a solubilizer, an osmotic pressure regulator, a coloring agent, and the like in a liquid formulation.

The compounds of the invention are suitable for administration routes such as oral administration, parenteral (intravenous, intramuscular or subcutaneous) administration, transdermal administration, translingual administration, or inhalation administration. Oral administration and parenteral (intravenous, intramuscular or subcutaneous) administration are preferred.

When orally administered, the compound of the invention may be prepared in any orally acceptable form, including, but not limited to a tablet, a pill, a pulvis, a syrup, a capsule, an aqueous solution, or an aqueous suspension, etc. The carriers for use in a tablet generally include lactose and maize starch. In addition, a lubricant such as magnesium stearate may also be added. Diluents for use in a capsule generally include lactose and dry maize starch. An aqueous suspension is generally obtained by mixing an active ingredient with a suitable emulsifying agent and a suitable suspending agent. If necessary, some sweetening agents, flavoring agents or coloring agents may be added to the oral formulation.

The compound of the invention may be administered in a form of a sterile formulation for injection, including a sterile injection water, an oil suspension or a sterile injection solution. The carriers and solvents used therein include water, Ringer's solution, and an isotonic sodium chloride solution. In addition, a sterile fixed oil can also be used as a solvent or a suspension medium, such as monoglyceride or diglyceride.

In addition, it has to be pointed out that the dosage of the compound of the invention, or the method of using the compound of the invention, depends on a lot of factors, including age, body weight, gender, general conditions of health, nutritional state, activity of a compound, administration time, metabolic rate, severity of a disease, and subjective judgment made by a physician. Preferably, the dosage used is between 0.001 and 100 mg/kg body weight/day, more preferably, the dosage is between 0.01 mg/kg and 50 mg/kg body weight/day, further more preferably, the dosage is between 0.1 mg/kg and 25 mg/kg body weight/day, and most preferably, the dosage is between 1 mg/kg and 10 mg/kg body weight/day. If necessary, an effective daily dose can be divided into multiple doses depending on the purpose of administration; therefore, a single-dose composition may comprise such a dose or a sub-dose thereof, so to form a daily dose. The administration frequency of the compound of Formula I can be determined by Physician's experiments and factors such as age, body weight, gender, general state of health, and type or severity of a disease; for example, the compound can be administered once a day, twice a day, three times a day, four times a day, five times a day, etc., or once every two days, once every three days, once every week, once every two weeks, etc.

The invention further provides use of the compound of Formula I or the pharmaceutically acceptable salt thereof according to the first aspect of the invention, or the pharmaceutical composition according to the third aspect of the invention in the manufacture of a medicament for treating or preventing a mental disorder or a nervous system disease.

The invention further provides a method for preparing or treating a mental disorder or a nervous system disease, comprising administering to a subject in need thereof an effective amount of the compound of Formula I or the pharmaceutically acceptable salt thereof according to the first aspect of the invention, or the pharmaceutical composition according to the third aspect of the invention.

In some preferred embodiments of the invention, the subject is a mammal, such as a bovine, an equine, a caprid, a suidae, a canine, a feline, a rodent, and a primate; and an especially preferred subject is human.

The invention further provides the compound of Formula I or the pharmaceutically acceptable salt thereof according to the first aspect of the invention, or the pharmaceutical composition according to the third aspect of the invention, for use in the prevention or treatment of a mental disorder or a nervous system disease.

In some preferred embodiments of the invention, the mental disorder is selected from the group consisting of schizophrenia, depression, manic depressive disorder (bipolar disorder), cognitive disorder, anxiety disorder, stress related disorder, attention deficit hyperactivity disorder, tic disorder, and mental disorder associated with organic lesion.

In some preferred embodiments of the invention, the mental disorder associated with organic lesion is selected from the group consisting of Alzheimer's disease, vascular dementia, mental disorder caused by brain trauma, mental disorder caused by intracranial infection, mental disorder caused by brain tumor, mental disorder caused by syphilis, epileptic mental disorder and mental disorder caused by HIV/AIDS.

In some preferred embodiments of the invention, the nervous system disease is selected from the group consisting of neurodegenerative disease (Alzheimer's disease, Parkinson's disease), cerebrovascular disease, brain trauma, spinal cord injury, demyelinating disease, multiple sclerosis, inflammatory demyelinating polyneuropathy, ischemic leukoencephalopathy, hypoxic leukoencephalopathy and diabetic neuropathy.

The invention further provides use of the compound of Formula I or the pharmaceutically acceptable salt thereof according to the first aspect of the invention, or the pharmaceutical composition according to the third aspect of the invention in the manufacture of an agent for inhibiting over-activation or proliferation of microglial cells.

In some preferred embodiments of the invention, the agent is used in an in vivo method.

In some preferred embodiments of the invention, the agent is used in an in vitro method.

In some preferred embodiments of the invention, the microglial cell is a cell line or from a subject.

The invention further provides the compound of Formula I or the pharmaceutically acceptable salt thereof according to the first aspect of the invention, or the pharmaceutical composition according to the third aspect of the invention, for use in inhibiting over-activation or proliferation of microglial cells.

In some preferred embodiments of the invention, the compound or the pharmaceutically acceptable salt thereof or the pharmaceutical composition is used in an in vivo method.

In some preferred embodiments of the invention, the compound or the pharmaceutically acceptable salt thereof or the pharmaceutical composition is used in an in vitro method.

In some preferred embodiments of the invention, the microglial cell is a cell line or from a subject.

The invention further provides a method for inhibiting over-activation or proliferation of microglial cells, comprising administering to cells an effective amount of the compound of Formula I or the pharmaceutically acceptable salt thereof according to the first aspect of the invention, or the pharmaceutical composition according to the third aspect of the invention.

In some preferred embodiments of the invention, the method is carried out in vivo.

In some preferred embodiments of the invention, the method is carried out in vitro.

In some preferred embodiments of the invention, the microglial cell is a cell line or from a subject.

The invention further provides use of the compound of Formula I or the pharmaceutically acceptable salt thereof according to the first aspect of the invention, or the pharmaceutical composition according to the third aspect of the invention in the manufacture of an agent for inhibiting the activity of dopamine receptor in a cell.

In some preferred embodiments of the invention, the dopamine receptor is dopamine D2 receptor.

In some preferred embodiments of the invention, the agent is used in an in vivo method.

In some preferred embodiments of the invention, the agent is used in an in vitro method.

In some preferred embodiments of the invention, the cell is a cell line or from a subject.

The invention further provides the compound of Formula I or the pharmaceutically acceptable salt thereof according to the first aspect of the invention, or the pharmaceutical composition according to the third aspect of the invention, for use in inhibiting the activity of dopamine receptor in a cell.

In some preferred embodiments of the invention, the dopamine receptor is dopamine D2 receptor.

In some preferred embodiments of the invention, the compound or the pharmaceutically acceptable salt thereof or the pharmaceutical composition is used in an in vivo method.

In some preferred embodiments of the invention, the compound or the pharmaceutically acceptable salt thereof or the pharmaceutical composition is used in an in vitro method.

In some preferred embodiments of the invention, the cell is a cell line or from a subject.

The invention further provides a method for inhibiting the activity of dopamine receptor in a cell, comprising administering to a cell an effective amount of the compound of Formula I or the pharmaceutically acceptable salt thereof according to the first aspect of the invention, or the pharmaceutical composition according to the third aspect of the invention.

In some preferred embodiments of the invention, the dopamine receptor is dopamine D2 receptor.

In some preferred embodiments of the invention, the method is carried out in vivo.

In some preferred embodiments of the invention, the method is carried out in in vitro.

In some preferred embodiments of the invention, the cell is a cell line or from a subject.

The invention further provides use of the compound of Formula I or the pharmaceutically acceptable salt thereof according to the first aspect of the invention, or the pharmaceutical composition according to the third aspect of the invention in the manufacture of an agent for enhancing the activity of NMDA receptor in a cell.

In some preferred embodiments of the invention, the agent is used in an in vivo method.

In some preferred embodiments of the invention, the agent is used in an in vitro method.

In some preferred embodiments of the invention, the cell is a cell line or from a subject.

The invention further provides the compound of Formula I or the pharmaceutically acceptable salt thereof according to the first aspect of the invention, or the pharmaceutical composition according to the third aspect of the invention, for use in enhancing the activity of NMDA receptor in a cell.

In some preferred embodiments of the invention, the compound or the pharmaceutically acceptable salt thereof or the pharmaceutical composition is used in an in vivo method.

In some preferred embodiments of the invention, the compound or the pharmaceutically acceptable salt thereof or the pharmaceutical composition is used in an in vitro method.

In some preferred embodiments of the invention, the cell is a cell line or from a subject.

The invention further provides a method for enhancing the activity of NMDA receptor in a cell, comprising administering to a cell an effective amount of the compound of Formula I or the pharmaceutically acceptable salt thereof according to the first aspect of the invention, or the pharmaceutical composition according to the third aspect of the invention.

In some preferred embodiments of the invention, the method is carried out in vivo.

In some preferred embodiments of the invention, the method is carried out in in vitro.

In some preferred embodiments of the invention, the cell is a cell line or from a subject.

The invention further provides use of the compound of Formula I or the pharmaceutically acceptable salt thereof according to the first aspect of the invention, or the pharmaceutical composition according to the third aspect of the invention in the manufacture of an agent for enhancing the content of myelin basic protein (MBP) in a cell, or reducing demyelination or pathological changes in white matter.

In some preferred embodiments of the invention, the agent is used in an in vivo method.

In some preferred embodiments of the invention, the agent is used in an in vitro method.

In some preferred embodiments of the invention, the cell is a cell line or from a subject.

The invention further provides the compound of Formula I or the pharmaceutically acceptable salt thereof according to the first aspect of the invention, or the pharmaceutical composition according to the third aspect of the invention, for use in enhancing the content of myelin basic protein (MBP) in a cell, or reducing demyelination or pathological changes in white matter.

In some preferred embodiments of the invention, the compound or the pharmaceutically acceptable salt thereof or the pharmaceutical composition is used in an in vivo method.

In some preferred embodiments of the invention, the compound or the pharmaceutically acceptable salt thereof or the pharmaceutical composition is used in an in vitro method.

In some preferred embodiments of the invention, the cell is a cell line or from a subject.

The invention further provides a method for enhancing the content of myelin basic protein (MBP) in a cell, or reducing demyelination or pathological changes in white matter, comprising administering to the cell an effective amount of the compound of Formula I or the pharmaceutically acceptable salt thereof according to the first aspect of the invention, or the pharmaceutical composition according to the third aspect of the invention.

In some preferred embodiments of the invention, the method is carried out in vivo.

In some preferred embodiments of the invention, the method is carried out in in vitro.

In some preferred embodiments of the invention, the cell is a cell line or from a subject.

The terms used in the invention are explained as follows. For a specific term, if the meanings in the invention are different from the meanings as generally understood by a person skilled in the art, the meanings in the invention will prevail; if no definition is made in the invention, it has the meanings as generally understood by a person skilled in the art. Unless otherwise specified, the terms used in the invention have the following meanings:

The term "$C_{1-6}$alkyl" used in the invention refers to a linear or branched alkyl having 1-6 carbon atoms, e.g. $C_{1-4}$alkyl, $C_{1-2}$alkyl, $C_1$alkyl, $C_2$alkyl, $C_3$alkyl, $C_4$alkyl, $C_5$alkyl or $C_6$alkyl. The particular examples include, but are not limited to methyl, ethyl, propyl, isopropyl, butyl, tert-butyl, pentyl, hexyl, etc.

The term "$C_{1-6}$alkoxy" used in the invention refers to a group having a structure of "$C_{1-6}$alkyl-O—", wherein $C_{1-6}$alkyl has the same meanings as defined above. For example, $C_{1-4}$alkoxy, $C_{1-2}$alkoxy, $C_1$alkoxy, $C_2$alkoxy, $C_3$alkoxy, $C_4$alkoxy, $C_5$alkoxy or $C_6$alkoxy. The particular examples include, but are not limited to methoxy, ethoxy, propoxy, isopropoxy, butoxy, tert-butoxy, pentoxy, hexoxy, etc.

The term "$C_{1-6}$alkylamino" used in the invention refers to a group having a structure of "$C_{1-6}$alkyl-NH—", wherein $C_{1-6}$alkyl has the same meanings as defined above. For example, $C_{1-4}$-alkylamino, $C_{1-2}$alkylamino, $C_1$alkylamino, $C_2$alkylamino, $C_3$alkylamino, $C_4$alkylamino, $C_5$alkylamino or $C_6$alkylamino. The particular examples include, but are not limited to methylamino, ethylamino, propylamino, isopropylamino, butylamino, tert-butylamino, pentylamino, hexylamino, etc.

The term "aryl" used in the invention refers to an aromatic carbocyclic group, which is monocyclic (e.g. phenyl), polycyclic (e.g. naphthyl), or is a fused ring having at least one aromatic ring (e.g. 1,2,3,4-tetrahydronaphthyl). For example, an aryl group containing 5-20 (e.g. 5-15 or 5-10) carbon atoms. The particular examples include, but are not limited to phenyl, naphthyl, anthryl, phenanthryl, fluorenyl, indenyl, acenaphthenyl, etc.

The term "heteroaryl" used in the invention refers to an aromatic cyclic group containing at least one and at most four heteroatoms selected from N, O and S. For example, 5-20 membered (e.g. 5-15 or 5-10) heteroaryl. The particular examples include, but are not limited to pyrrolyl, furyl, thienyl, imidazolyl, pyrazolyl, oxazolyl, isoxazolyl, thiazolyl, isothiazolyl, triazolyl, pyridyl, pyranyl, pyrimidinyl, pyrazinyl, pyridazinyl, triazinyl, indolyl, benzofuryl, benzothienyl, benzoimidazolyl, benzopyrazolyl, benzoxazolyl, benzisoxazolyl, benzothiazolyl, benzoisothiazolyl, benzotriazolyl, quinolyl, benzopyranyl, benzopyrimidinyl, quinoxalinyl, benzopyridazinyl, benzotriazinyl, purinyl, etc.

The term used in the invention "a saturated or partially saturated alkylene" refers to a group derived from the removal of two hydrogen atoms from a saturated or partially saturated alkyl, for example, a saturated or partially saturated alkylene containing 2-6 carbon atoms, e.g. alkylene containing 2-6 carbon atoms, e.g. alkylene containing 2-4 carbon atoms. The particular examples include, but are not limited to methylene, ethylene, propylene, butylene, 1,2-ethylene, 1,3-propylene, 1,4-butylene, 1,5-pentylene, 1,6-hexylene, etc.

The term "halogen" used in the invention include fluorine, chlorine, bromine and iodine.

The compound of the invention may have a chiral center, and may be present in the form of different enantiomers and diastereomer. All of the optical isomers and racemic mixtures of the compound of the invention fall into the protection scope of the invention.

The term "pharmaceutically acceptable" used in the invention generally means that a substance is pharmaceutically or medically useful, or although cannot be used directly in pharmaceutics or medicine, the substance can be used as an intermediate for the preparation of a pharmaceutical or medical product, and is finally removed by a suitable method before being used in pharmaceutics or medicine. For example, a pharmaceutically acceptable salt not only includes a pharmaceutical salt that may be used in clinic, but also a salt that may be used in the preparation of the compound of the invention and can be removed in the subsequent process. The term "a pharmaceutically acceptable salt" used in the invention includes a salt formed by the reaction with a pharmaceutically acceptable inorganic acid, organic acid, inorganic base, or organic base, and a salt formed by the reaction of a quaternary ammonium and an acid. Suitable examples of acid addition salts include, but are not limited to hydrochloride, hydrobromide, sulfate, phosphate, nitrate, perchlorate, fumarate, acetate, propionate, pyruvate, succinate, glycolate, formate, lactate, maleate, tartrate, citrate, pamoate, malonate, glutarate, hydroxyl maleate, phenylacetate, glutamate, benzoate, salicylate, fumarate, tosylate, mesylate, naphthalene-2-sulfonate, benzenesulfonate, hydroxynaphthoate, hydroiodide, malate, stearate, tannate, etc. Although other acid addition salts such as oxalate are not pharmaceutically acceptable, they can be used to prepare salts as intermediates, so as to obtain the compound and a pharmaceutically acceptable salt thereof according to the invention. Particular examples of suitable base salts include sodium salt, lithium salt, potassium salt, magnesium salt, aluminum salt, calcium salt, zinc salt, ammonium salt, triethylamine salt, tert-butylamine salt, N,N'-dibenzylethylenediamine salt, procaine salt, chloroprocaine salt, choline salt, diethanolamine salt, ethylene diamine salt, N-methylglucosamine salt, etc.

In the embodiments of the invention, the subject is a mammal, such as a bovine, an equine, a caprid, a suidae, a canine, a feline, a rodent, and a primate; and an especially preferred subject is human.

The term "an effective amount" used in the invention refers to an amount that is sufficient to achieve or at least partially achieve a desired effect. For example, a prophylactically effective amount refers to an amount that is sufficient to prevent, suppress or delay the development of a disease; a therapeutically effective amount refers to an amount that is sufficient to cure or at least partially suppress a disease and its complications in a patient with the disease. The determination of such an effective amount is completely within the ability of a person skilled in the art. For example, an amount effective for a therapeutic use depends on the severity degree of a disease to be treated, general state of the immune system in a patient, general conditions of a patient, such as age, body weight and gender, administration means of drugs, additional therapies used simultaneously, and the like.

BENEFICIAL EFFECTS OF THE INVENTION

In the invention, a class of novel compounds is obtained through modification of flavanones. The compounds can simultaneously act on multiple targets such as dopaminergic system, glutamatergic system, microglial cells and brain white matter. In some embodiments of the invention, the compounds exert significant activity of inhibiting microglial activation and neuroinflammation, can antagonize dopamine D2 receptor, improve the ethological change in multiple animal models for mental disorders, and effectively inhibit neuroinflammation and demyelination. It is indicated that the compounds of the invention can improve cognitive function, and prevent or treat a mental disorder or a nervous system disease. The invention provides a new concept for the treatment of relevant diseases.

SPECIFIC MODES FOR CARRYING OUT THE INVENTION

Figure 1:
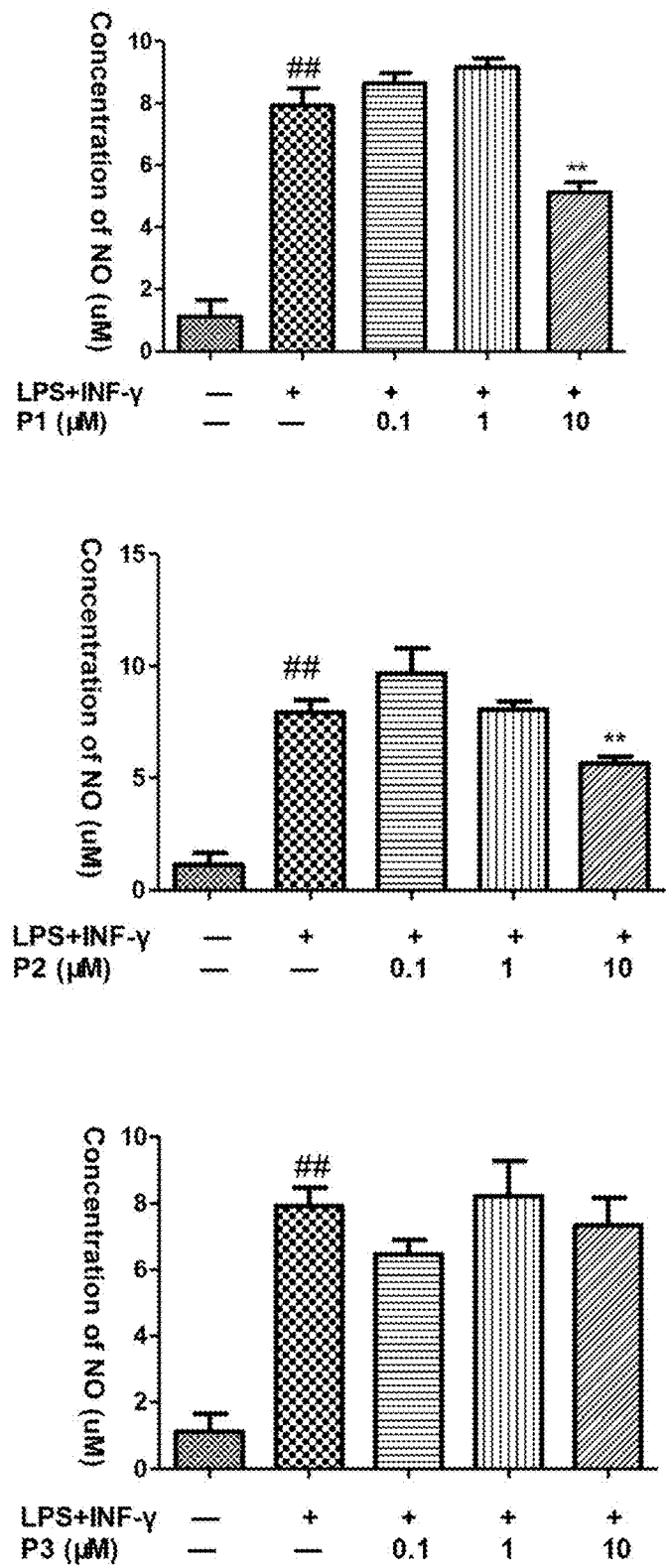
FIG. 1 shows the result of the compounds of the invention for the inhibition of LPS+INF-γ-induced activation of microglial cells (BV2 cells) and over-production and release of nitrogen monoxide (NO), wherein each concentration for each sample was repeated in 6 parallel wells, the experiment was repeated twice, and the data was expressed as Mean±SE; $^{\#\#}P<0.01$, the model group was compared with the control group; $*P<0.05$, $**P<0.01$, the drug group was compared with the model group.
Figure 1:
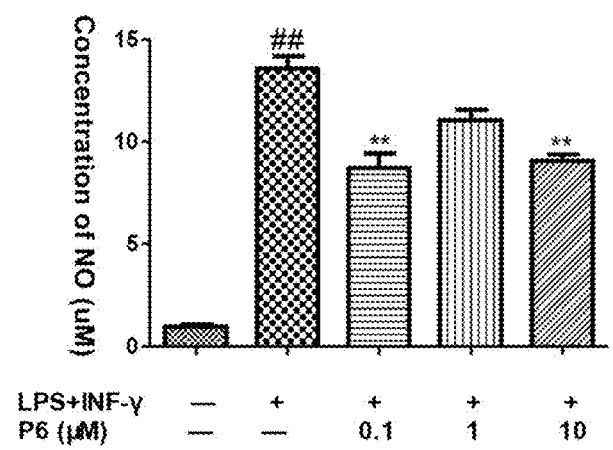
Figure 1:
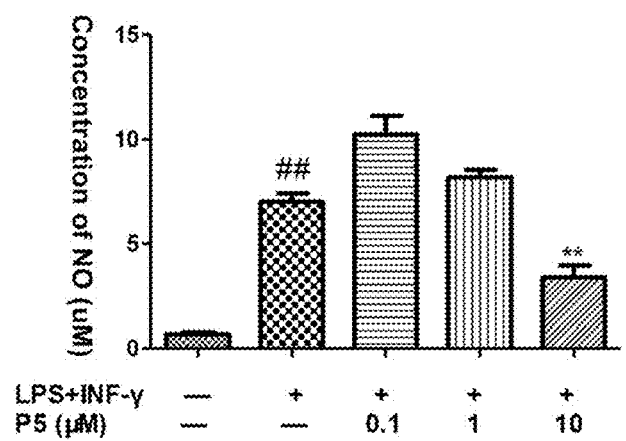
Figure 1:
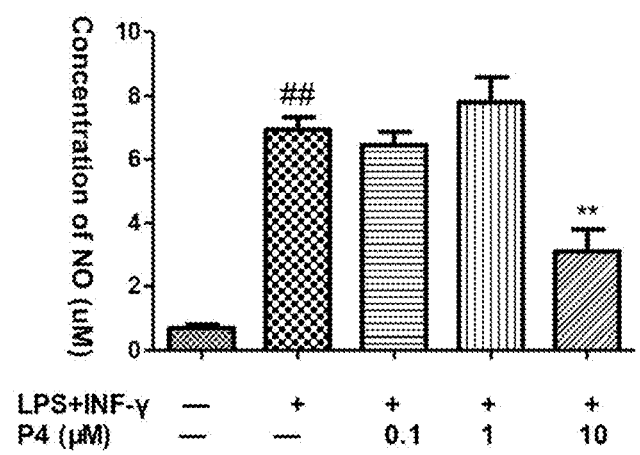
Figure 1:
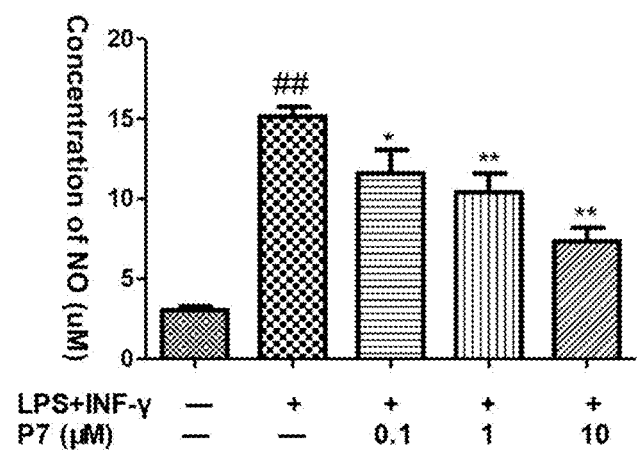

The embodiments of the invention are illustrated in detail by reference to the following examples. However, it is understood by those skilled in the art that the examples are used only for the purpose of illustrating the invention, rather than limiting the protection scope of the invention. In the case where the concrete conditions are not indicated in the examples, the examples are carried out according to conventional conditions or the conditions recommended by the manufacturer. The reagents or instruments used, for which the manufacturers are not indicated, are conventional products that can be purchased on the market or prepared by the well-known teachings.

The structures of the compounds in the Examples are determined by conventional spectroscopic techniques (Infrared Spectrum, Ultraviolet Spectrum, Nuclear Magnetic Resonance or ESI-MS).

A. Synthesis of the Compounds of the Invention

EXAMPLE 1

Synthesis of 5-hydroxy-2-(4-methoxyphenyl)-7-(4-(4-(2-methoxyphenyl)-piperazin-1-yl)-butoxy)-chroman-4-one (P1)

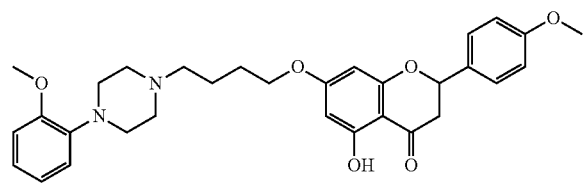 [SMILES: COc1ccc(C2CC(=O)c3c(O)cc(OCCCCN4CCN(c5ccccc5OC)CC4)cc3O2)cc1]

1) Phloroglucinol (5.0 g, 40 mmol) was dissolved in a solution of carbon disulfide (50 ml) and nitrobenzene (15 ml), and anhydrous aluminium chloride (15.6 g, 120 mmol) was added. After stirring at room temperature for 10 min, a solution (10 ml) of acetyl chloride (4.23 ml, 60 mmol) in carbon disulfide was added to the reaction solution. The resultant solution was then heated to reflux at 50° C. for 1 h. Carbon disulfide was removed by distillation under reduced pressure. Hydrochloric acid (10 ml) and an ice-water mixture (50 ml) were added to the residue, and the resultant solution was extracted with ethyl acetate for 3 times (50 ml×3). The organic phase was washed with saturated sodium chloride solution, and dried with anhydrous sodium sulfate, and ethyl acetate was removed by distillation under reduced pressure. The resultant residue was mixed with silica gel, and purified by silica gel column. The column was eluted with petroleum ether: ethyl acetate (2:1), to obtain a light yellow solid (5.71 g, yield: 85.7%).

2) The product (5.0 g) obtained in the step 1) was dissolved in acetone (50 ml), and anhydrous potassium carbonate (15 g) was added. Chloromethyl methyl ether (1.58 ml) was slowly added dropwise at room temperature within 20 min. The resultant mixture was then further stirred at room temperature for 2 h. Anhydrous potassium carbonate solid was filtered off, and acetone solution was removed by distillation under reduced pressure. Water (20 ml) was added to the residue, and the resultant solution was extracted with ethyl acetate for 3 times (30 ml×3). The organic phase was washed with saturated sodium chloride solution, and dried with anhydrous sodium sulfate. The organic solvent was removed by distillation under reduced pressure. The residue was mixed with silica gel, and purified by silica gel column. The column was eluted with petroleum ether: ethyl acetate (15:1), to obtain a light yellow oil (about 4.3 g, yield: 56.4%).

3) The product (4 g) obtained in the step 2), sodium hydroxide (10 g), methanol (100 ml), and p-methoxybenzaldehyde (3.64 ml) were heated to reflux for 5 h, and cooled to room temperature. The solvent was removed by distillation under reduced pressure, distilled water (50 ml) was added, and the resultant solution was neutralized with 2% HCl. The resultant solution was extracted with ethyl acetate for 3 times (50 ml×3), the organic phase was washed with saturated sodium chloride solution, and dried with anhydrous sodium sulfate. Ethyl acetate was removed by distillation under reduced pressure. The residue was mixed with silica gel, and purified by silica gel column. The column was washed with 5 column volumes of petroleum ether, and then eluted with petroleum ether: ethyl acetate (10:1), to obtain a yellow solid (4.98 g, yield: 85.2%).

$^1$H NMR (300 MHz, DMSO-d$_6$): δ=12.39 (br s, 1H, OH-5), 7.67 (d, 2H, J=8.7 Hz, Ar—H), 7.53 (d, 2H, J=9.6 Hz, Ar—H), 7.01 (d, 2H, J=9.0 Hz, Ar—H), 5.28 (s, 2H, —OCH$_2$—), 5.22 (s, 2H, —OCH$_2$—), 3.81 (s, 3H, —OCH$_3$), 3.40 (s, 3H, —OCH$_3$), 3.40 (s, 3H, —OCH$_3$).

4) The product (2 g) obtained in the step 3), sodium acetate (8 g), and methanol (30 ml) were heated to reflux for 12 h, and cooled to room temperature. The solvent was removed by distillation under reduced pressure, distilled water (30 ml) was added, and the result solution was extracted with ethyl acetate for 3 times (20 ml×3). The organic phase was washed with saturated sodium chloride solution, and dried with anhydrous sodium sulfate. Ethyl acetate was removed by distillation under reduced pressure. The residue was mixed with silica gel, and purified by silica gel column. The column was eluted with 4 column volumes of petroleum ether: ethyl acetate (10:1), and then eluted with petroleum ether: ethyl acetate (3:1), to obtain a colorless oil (1.63 g, yield: 81.5%).

¹H NMR (300 MHz, DMSO-d₆): δ=7.44 (d, 2H, J=8.7 Hz, Ar—H), 6.97 (d, 2H, J=8.7 Hz, Ar—H), 6.36 (d, 1H, J=2.1 Hz, H-8), 6.33 (d, 1H, J=2.4 Hz, H-6), 5.50 (dd, 1H, J=12.9, 2.7 Hz, H-2), 5.23 (s, 2H, —OCH₂—), 5.22 (s, 2H, —OCH₂—), 3.77 (s, 3H, —OCH₃), 3.41 (s, 3H, —OCH₃), 3.38 (s, 3H, —OCH₃), 3.14 (dd, 1H, J=16.2, 12.9 Hz, H-3α), 2.60 (dd, 1H, J=16.2, 2.7 Hz, H-3β).

5) The product (1.5 g) obtained in the step 4), methanol (30 ml), and concentrated hydrochloric acid (1 ml) were heated to reflux for 30 min, and cooled to room temperature. The solvent was removed by distillation under reduced pressure, and the residue was suspended in a small amount of methanol, and poured into an ice-water mixture (100 ml). The resultant mixture was filtrated under reduced pressure, and the filter cake was oven-dried to obtain a white solid (0.87 g, yield: 72.3%).

¹H NMR (300 MHz, DMSO-d₆): δ=12.14 (br s, 1H, OH-5), 10.78 (br s, 1H, OH-7), 7.44 (d, 2H, J=8.7 Hz, Ar—H), 6.97 (d, 2H, J=8.7 Hz, Ar—H), 5.90 (br s, 1H, H-8), 5.89 (br s, 1H, H-6), 5.50 (dd, 1H, J=12.6, 2.7 Hz, H-2), 3.77 (s, 3H, —OCH₃), 3.28 (dd, 1H, J=14.1, 12.6 Hz, H-3α), 2.72 (dd, 1H, J=14.1, 3.0 Hz, H-3β).

6) The product (0.8 g) obtained in the step 5), anhydrous potassium carbonate (3 g), acetone (20 ml), and 1,4-dibromobutane (1.2 g) were heated to reflux for 3 h, and cooled to room temperature. The anhydrous potassium carbonate solid was filtered off. The organic phase was mixed with silica gel, and purified by silica gel column. The column was eluted with petroleum ether: ethyl acetate (15:1), to obtain a yellow oil (0.61 g, yield: 54.5%).

ESI+-MS: 423.1 [M+H]⁺

¹H NMR (300 MHz, CDCl₃): δ=12.03 (br s, 1H, OH-5), 7.40 (d, 2H, J=8.7 Hz, Ar—H), 6.97 (d, 2H, J=8.7 Hz, Ar—H), 6.06 (d, 1H, J=2.4 Hz, H-8), 6.04 (d, 1H, J=2.4 Hz, H-6), 5.38 (dd, 1H, J=12.9, 3.0 Hz, H-2), 4.04 (t, 2H, J=6.0 Hz, H-1"), 3.85 (s, 3H, —OCH3), 3.49 (t, 2H, J=6.0 Hz, H-4"), 3.11 (dd, J=17.1, 12.9 Hz, H-3α), 2.80 (dd, 1H, J=17.1, 3.0 Hz, H-3β), 2.68 (m, 4H, H₂-2'''; Hz-6'''), 2.49 (t, 2H, J=7.2 Hz, H-5'''), 2.09 (m, 2H, H-3"), 1.96 (m, 2H, H-2").

7) The product (0.6 g) obtained in the step 6), anhydrous potassium carbonate (2 g), potassium iodide (0.5 g), acetonitrile (10 ml), and 1-(2-methoxyphenyl)piperazine (0.68 g) were heated to reflux for 2 h, and cooled to room temperature. The anhydrous potassium carbonate solid was filtered off. The organic phase was mixed with silica gel, and purified by silica gel column. The column was eluted with petroleum ether: ethyl acetate (2:1) to obtain a yellow oil (0.15 g, yield: 19.7%).

ESI⁺-MS: 532.9 [M +H]⁺

HR-Q-TOF-MS: 533.2712 [M+H]⁺(calcd for C₃₁H₃₆N₂O₆, 533.2646).

¹H NMR (300 MHz, CDCl₃): δ=12.04 (br s, 1H, OH-5), 7.40 (d, 2H, J=8.7 Hz, Ar—H), 6.90 (m, 6H, Ar—H), 6.08 (d, 1H, J=2.1 Hz, H-8), 6.05 (br s, 1H, J=1.8 Hz, H-6), 5.38 (dd, 1H, J=12.9, 2.7 Hz, H-2), 4.03 (t, 2H, J=6.0 Hz, H-1"), 3.88 (s, 3H, —OCH₃), 3.85 (s, 3H, —OCH₃), 3.11 (m, 5H, H₂-4"; H₂-3"; H-3α), 2.80 (dd, 1H, J=17.1, 3.0 Hz, H-3β), 2.68 (m, 4H, H₂-2'''; H₂-6'''), 2.49 (t, 2H, J=7.2 Hz, H-5'''), 1.85 (m, 2H, H-2"), 1.70 (m, 2H, H-3"). ¹³C NMR (300 MHz, CDCl3): δ=195.9 (C-4), 167.5 (C-7), 164.1 (C-7'''), 162.9 (C-5), 160.1 (C-4'), 152.3 (C-9), 141.4 (C-8'''), 130.5 (C-1'), 127.7 (C-2', 6'), 122.9 (C-12'''), 121.0 (C-10'''), 118.2 (C-11'''), 114.2 (C-3', 5'), 111.3 (C-9'''), 103.1 (C-10), 95.6 (C-6), 94.6 (C-8), 79.0 (C-2), 68.3 (C-1"), 58.1 (C-4"), 55.4 (2x-OCH₃), 53.4 (C-3''', 5'''), 50.6 (C-2''', 6'''), 43.2 (C-3), 27.0 (C-2"), 23.2 (C-3").

EXAMPLE 2

Synthesis of 5-hydroxy-2-(4-methylphenyl)-7-(4-(4-(2-methoxyphenyl)-piperazin-1-yl)-butoxy)-chroman-4-one (P2)

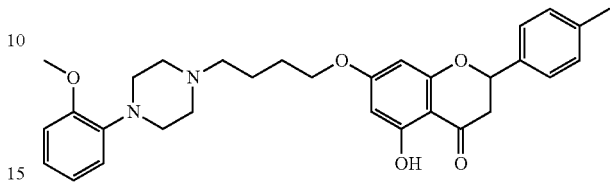

The operations were the same as those described in Example 1, and in the step 3), p-methylbenzaldehyde was used as a reactant.

ESI+-MS: 517.2 [M +H]⁺

HR-Q-TOF-MS: 517.2766 [M+H]⁺ (calcd for C₃₁H₃₆N₂O₅, 517.2697).

¹H NMR (300 MHz, CDCl₃): δ=12.03 (br s, 1H, OH-5), 7.36 (d, 2H, J=8.1 Hz, Ar—H), 7.26 (d, 2H, J=7.8 Hz, Ar—H),6.95 (m, 4H, Ar—H), 6.08 (d, 1H, J=2.7 Hz, H-8), 6.06 (br s, 1H, J=2.4 Hz, H-6), 5.40 (dd, 1H, J=12.9, 3.0 Hz, H-2), 4.03 (t, 2H, J=6.3 Hz, H-1"), 3.88 (s, 3H, —OCH₃), 3.10 (m, 5H, H₂-4"; H₂-3'''; H-3α), 2.82 (dd, 1H, J=17.1, 3.0 Hz, H-3β), 2.69 (m, 4H, H₂-2'''; Hz-6'''), 2.49 (t, 2H, J=7.2 Hz, H-5'''), 2.40 (s, 3H, —CH₃), 1.83 (m, 2H, H-2"), 1.71 (m, 2H, H-3"). ¹³C NMR (300 MHz, CDCl₃): δ=195.8 (C-4), 167.5 (C-7), 164.1 (C-7'''), 162.9 (C-5), 152.3 (C-9), 141.4 (C-8'''), 138.8 (C-4'), 135.5 (C-1'), 129.5 (C-2', 6'), 126.2 (C-3', 5'), 122.9 (C-12'''), 121.0 (C-10'''), 118.2 (C-11'''), 111.3 (C-9'''), 103.1 (C-10), 95.6 (C-6), 94.6 (C-8), 79.1 (C-2), 68.3 (C-1"), 58.1 (C-4"), 55.4 (2-OCH₃), 53.4 (C-3''', 5'''), 50.6 (C-2''', 6'''), 43.3 (C-3), 27.0 (C-2"), 23.2 (C-3"), 21.2 (—CH₃).

EXAMPLE 3

Synthesis of 5-hydroxy-2-(4-fluorophenyl)-7-(4-(4-(2-methoxyphenyl)-piperazin-1-yl)-butoxy)-chroman-4-one (P3)

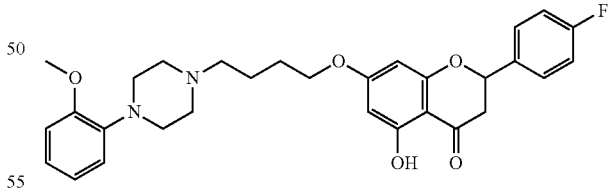

The operations were the same as those described in Example 1, p-fluorobenzaldehyde was used as a reactant in the step 3), and the product P3 was a yellow oil.

ESI+-MS: 520.8 [M+H]⁺

HR-Q-TOF-MS: 521.2506 [M+H]⁺ (calcd for C₃₀H₃₃FN₂O₅, 521.2446).

¹H NMR (300 MHz, CDCl₃): δ=12.01 (br s, 1H, OH-5), 7.45 (m, 2H, Ar—H), 7.16 (m, 2H, J=7.8 Hz, Ar—H),6.95 (m, 4H, Ar—H), 6.10 (d, 1H, J=2.4 Hz, H-8), 6.06 (d, 1H, J=2.1 Hz, H-6), 5.40 (dd, 1H, J=13.2, 3.0 Hz, H-2), 4.03 (t,

2H, J=6.0 Hz, H-1"), 3.88 (s, 3H, —OCH3), 3.06 (m, 5H, H$_2$-4"; Hz-3"'; H-3α), 2.82 (dd, 1H, J=17.1, 3.3 Hz, H-3β), 2.68 (m, 4H, H$_2$-2"'; Hz-6"'), 2.49 (t, 2H, J=7.5 Hz, H-5"'), 2.40 (s, 3H, —CH$_3$), 1.82 (m, 2H, H-2"), 1.70 (m, 2H, H-3"). $^{13}$C NMR (300 MHz, CDCl3): δ=195.3 (C-4), 167.6 (C-7), 164.2 (C-7"), 162.6 (C-5), 152.3 (C-9), 141.4 (C-8"'), 134.4 (C-4'), 134.3 (C-1'), 128.0 (C-2', 6'), 122.9 (C-12"'), 121.0 (C-10"'), 118.2 (C-11"'), 116.0 (C-3'), 115.7 (C-3'), 111.3 (C-9"'), 103.0 (C-10), 95.7 (C-6), 94.7 (C-8), 78.5 (C-2), 68.3 (C-1"), 58.1 (C-4"), 55.4 (2-OCH$_3$), 53.5 (C-3"', 5"), 50.6 (C-2"', 6"'), 43.4 (C-3), 27.0 (C-2"), 23.2 (C-3").

EXAMPLE 4

Synthesis of 5-hydroxy-2-(4-methoxyphenyl)-7-(4-(4-(2-methoxyphenyl)-piperazin-1-yl)-propoxy)-chroman-4-one (P6)

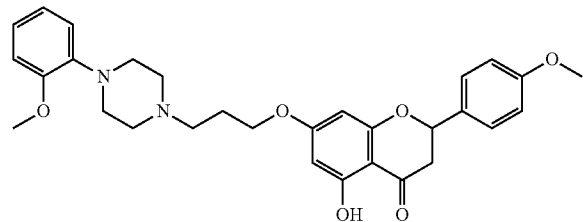 [SMILES: COc1ccc(C2CC(=O)c3c(O)cc(OCCCN4CCN(c5ccccc5OC)CC4)cc3O2)cc1]

The operations were the same as those described in Example 1, 1,3-dibromopropane was used as an reactant in the step 6), and the product P3 was a yellow oil.

ESI+-MS: 519.0 [M+H]$^+$

HR-Q-TOF-MS: 519.2548 [M+H]$^+$ (calcd for C$_{30}$H$_{34}$N$_2$O$_6$, 519.2490).

$^1$H NMR (300 MHz, CDCl$_3$): δ=12.04 (br s, 1H, OH-5), 7.40 (d, 2H, J=8.4 Hz, Ar—H), 6.96 (m, 6H, Ar—H), 6.09 (br s, 1H, H-8), 6.08 (br s, 1H, H-6), 5.38 (dd, 1H, J=12.9, 2.4 Hz, H-2), 4.08 (t, 2H, J=6.0 Hz, H-1"), 3.88 (s, 3H, —OCH3), 3.85 (s, 3H, —OCH$_3$), 3.11 (m, 5H, Hz-3"; Hz-3"'; H-3α), 2.80 (dd, 1H, J=17.1, 3.0 Hz, H-3β), 2.69 (m, 4H, H$_2$-2"'; H$_2$-6"'), 2.58 (t, 2H, J=7.2 Hz, H-5"'), 2.03 (m, 2H, H-2"). $^{13}$C NMR (300 MHz, CDCl$_3$): δ=196.0 (C-4), 167.2 (C-7), 164.1 (C-7"'), 162.9 (C-5), 160.1 (C-4'), 152.2 (C-9), 140.8 (C-8"'), 130.4 (C-1'), 127.7 (C-2', 6'), 123.3 (C-12"'), 121.1 (C-10"'), 118.4 (C-11"'), 114.2 (C-3', 5'), 111.2 (C-9"'), 103.2 (C-10), 95.6 (C-6), 94.6 (C-8), 79.0 (C-2), 66.4 (C-1"), 55.4 (2×-OCH$_3$), 54.8 (C-3"), 53.2 (C-5"', 9"), 49.8 (C-2"', 6"'), 43.2 (C-3), 29.7 (C-2").

EXAMPLE 5

Synthesis of 5-hydroxy-2-(4-methoxyphenyl)-7-(4-(4-(6-fluoro-benzo[d]isoxazol-3-yl)-piperidin-1-yl)-butoxy)-chroman-4-one (P5)

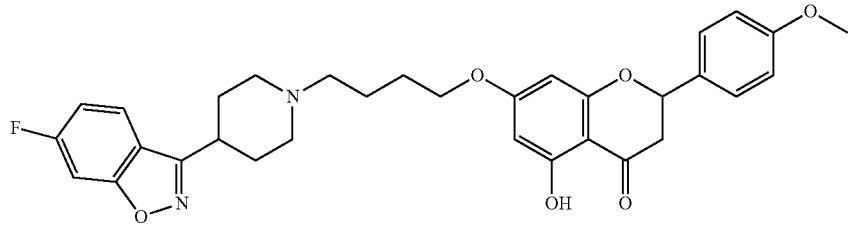 [SMILES: COc1ccc(C2CC(=O)c3c(O)cc(OCCCCN4CCC(c5noc6cc(F)ccc56)CC4)cc3O2)cc1]

The operations were the same as those described in Example 1, 6-fluoro-3-(4-piperidinyl)-1,2-benzisoxazole was used as an reactant in the step 7), and the product P5 was a yellow oil.

ESI+-MS: 560.8 [M+H]$^+$

HR-Q-TOF-MS: 561.2447 [M+H]$^+$ (calcd for C$_{32}$H$_{33}$FN$_2$O$_6$, 561.2395).

$^1$H NMR (300 MHz, CDCl$_3$): δ=12.05 (br s, 1H, OH-5), 7.40 (dd, 1H, J=8.7, 5.1 Hz, Ar—H), 7.44 (d, 2H, J=8.7 Hz, Ar—H), 7.25 (dd, 2H, J=8.7, 2.1 Hz, Ar—H), 7.07 (dt, 1H, J=9.0, 2.1 Hz, Ar—H), 6.97 (d, 2H, J=8.7 Hz, Ar—H), 6.08 (d, 1H, J=2.1 Hz, H-8), 6.06 (br s, 1H, J=2.4 Hz, H-6), 5.40 (dd, 1H, J=13.2, 3.0 Hz, H-2), 4.03 (t, 2H, J=6.0 Hz, H-1"), 3.85 (s, 3H, —OCH$_3$), 3.12 (m, 4H, H$_2$-4"; H-8"; H-3α), 2.81 (dd, 1H, J=17.1, 3.0 Hz, H-3β), 2.47 (t, 2H, J=7.2 Hz, H-6"), 2.08 (m, 6H, H$_2$-7"; H$_2$-9"; H$_2$-10"), 1.83 (m, 2H, H-2"), 1.70 (m, 2H, H-3"). $^{13}$C NMR (300 MHz, CDCl3): δ=195.9 (C-4), 167.5 (C-7), 164.1 (C-6"'), 162.9 (C-5), 161.1 (C-9), 160.1 (C-4'), 130.5 (C-1'), 127.7 (C-2', 6'), 122.7 (C-8"'), 122.5 (C-6"'), 117.3 (C-3"'), 114.4 (C-3', 5'), 112.5 (C-9"'), 112.1 (C-9"'), 103.1 (C-10), 97.6 (C-7"'), 97.2 (C-7"'), 95.5 (C-6), 94.6 (C-8), 79.0 (C-2), 68.3 (C-1"), 58.3 (C-4"), 55.4 (—OCH$_3$), 53.5 (C-6", 10"), 43.2 (C-3), 34.6 (C-8"), 30.5 (C-7", 9"), 27.0 (C-2"), 23.3 (C-3").

EXAMPLE 6

Synthesis of 5-hydroxy-2-(4-fluorophenyl)-7-(4-(4-(6-fluoro-benzo[d]isoxazol-3-yl)-piperidin-1-yI)-butoxy)-chroman-4-one (P4)

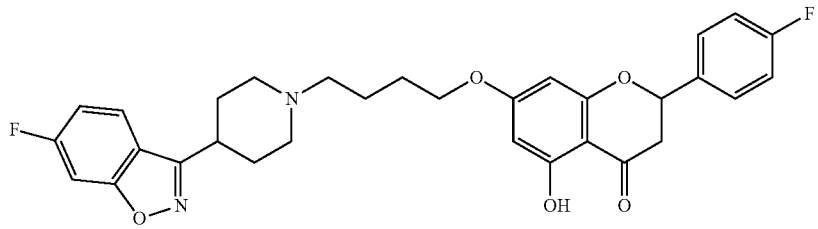 [SMILES: O=C1CC(c2ccc(F)cc2)Oc2cc(OCCCCN3CCC(c4noc5cc(F)ccc45)CC3)cc(O)c21]

The operations were the same as those described in Example 1, p-fluorobenzaldehyde was used as a reactant in the step 3), 6-fluoro-3-(4-piperidinyl)-1,2-benzisoxazole was used as an reactant in the step 7), and the product was a yellow oil.

ESI+-MS: 548.8 [M+H]$^+$

HR-Q-TOF-MS: 549.2273 [M+H]$^+$ (calcd for $C_{31}H_{30}F_2N_2O_5$, 549.2196).

$^1$H NMR (300 MHz, CDCl$_3$): δ=12.04 (br s, 1H, OH-5), 7.40 (dd, 2H, J=8.7, 5.1 Hz, Ar—H), 7.44 (m, 2H, Ar—H), 7.24 (dd, 2H, J=8.7, 2.1 Hz, Ar—H), 7.09 (m, 4H, Ar—H), 6.08 (d, 1H, J=2.1 Hz, H-8), 6.05 (br s, 1H, J=2.4 Hz, H-6), 5.40 (dd, 1H, J=12.6, 3.0 Hz, H-2), 4.03 (t, 2H, J=6.0 Hz, H-1''), 3.06 (m, 4H, Hz-4''; H-8''; H-3α), 2.80 (dd, 1H, J=17.1, 3.0 Hz, H-3β), 2.48 (t, 2H, J=7.2 Hz, H-6''), 2.05 (m, 6H, H$_2$-7''; H$_2$-9''; H$_2$-10''), 1.83 (m, 2H, H-2''), 1.70 (m, 2H, H-3''). $^{13}$C NMR (300 MHz, CDCl$_3$): δ=195.9 (C-4), 167.5 (C-7), 164.1 (C-4'''), 162.6 (C-5), 161.0 (C-9), 134.3 (C-4'), 134.3 (C-1'), 128.0 (C-2', 6'), 122.7 (C-8'''), 122.5 (C-6'''), 117.3 (C-9'''), 115.9 (C-3'), 115.7 (C-3'), 112.5 (C-1'''), 112.1 (C-7'''), 103.0 (C-10), 97.2 (C-5'''), 95.7 (C-6), 94.6 (C-8), 78.5 (C-2), 68.3 (C-1''), 58.2 (C-4''), 53.4 (C-6'', 10''), 30.4 (C-7'', 9''), 43.3 (C-3), 34.5 (C-8''), 26.9 (C-2''), 23.2 (C-3'').

EXAMPLE 7

Synthesis of 5-hydroxy-2-(4-methoxyphenyl)-7-(4-(4-(6-fluoro-benzo[d]isoxazol-3-yl)-piperidin-1-yl)-propoxy)-chroman-4-one (P7)

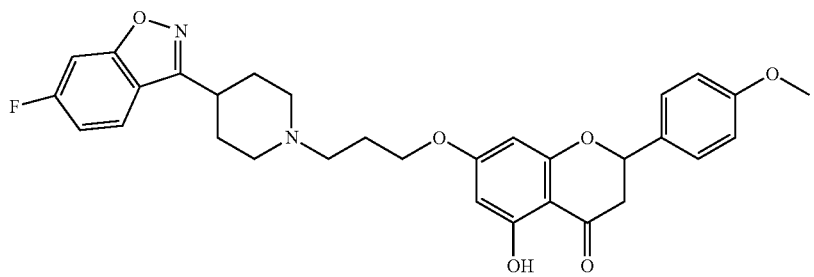 [SMILES: COc1ccc(C2CC(=O)c3c(O)cc(OCCCN4CCC(c5noc6cc(F)ccc56)CC4)cc3O2)cc1]

The operations were the same as those described in Example 1, 1,3-dibromopropane was used as an reactant in the step 6), 6-fluoro-3-(4-piperidinyl)-1,2-benzisoxazole was used as an reactant in the step 7), and the product was a yellow oil.

ESI+-MS: 546.9 [M+H]$^+$

HR-Q-TOF-MS: 547.2309 [M+H]$^+$ (calcd for $C_{31}H_{31}FN_2O_6$, 547.2239).

$^1$H NMR (300 MHz, CDCl$_3$): δ=12.04 (br s, 1H, OH-5), 7.72 (dd, 1H, J=8.4, 5.1 Hz, Ar—H), 7.39 (d, 2H, J=8.4 Hz, Ar—H), 7.25 (m, 1H, Ar—H), 7.06 (dt, 1H, J=9.0, 2.1 Hz, Ar—H), 6.96 (d, 2H, J=8.4 Hz, Ar—H), 6.10 (br s, 1H, H-8), 6.08 (br s, 1H, H-6), 5.40 (dd, 1H, J=12.9, 2.1 Hz, H-2), 4.08 (t, 2H, J=6.0 Hz, H-1''), 3.84 (s, 3H, —OCH$_3$), 3.11 (m, 4H, H$_2$-3''; H-8''; H-3α), 2.81 (dd, 1H, J=17.1, 2.7 Hz, H-3β), 2.60 (t, 2H, J=7.2 Hz, H-5''), 2.09 (m, 8H, H$_2$-2''; H$_2$-6''; H$_2$-8''; H$_2$-9''). $^{13}$C NMR (300 MHz, CDCl3): δ=196.0 (C-4), 167.4 (C-7), 164.1 (C-6''), 162.9 (C-5), 161.0 (C-9), 160.0 (C-4'), 130.4 (C-1'), 127.7 (C-2', 6'), 122.7 (C-8'''), 122.6 (C-6'''), 117.3 (C-3'''), 114.2 (C-3', 5'), 112.5 (C-9'''), 112.2 (C-9'''), 103.1 (C-10), 97.6 (C-7'''), 95.6 (C-6), 94.6 (C-8), 79.0 (C-2), 66.7 (C-1''), 55.4 (—OCH$_3$), 55.0 (C-3''), 53.5 (C-5'', 9''), 43.2 (C-3), 34.5 (C-7''), 30.4 (C-6'', 8''), 30.0 (C-2''), 26.5 (C-3'').

B. Pharmacological Study on the Compounds of the Invention

EXPERIMENTAL EXAMPLE 1

Effects of the Compounds of the Invention on LPS+INF-γ-Induced Inflammatory Response in Microglial Cells Objective: microglial activation and neuroinflammation are the important pathogenic mechanisms of many central nervous system diseases. Inflammation-inducing substances, bacterial endotoxin (lipopolysaccharide (LPS)) and interferon-γ (IFN-γ), can stimulate the production of pre-inflammatory cytokines in an organism which trigger an inflammatory cascade, and further activate inflammatory cells such as microglial cells, to release inflammatory mediators such as nitrogen monoxide (NO), thereby forming an inflammatory network. In this experiment, the novel compounds synthesized in the invention were studied for their inhibitory effects on inflammation in microglial cells, by establishing an LPS+INF-γ-induced inflammation model in microglial cells (BV2 cells).

Methods: BV2 cells (mouse microglial cell line) in exponential growth phase were seeded on a 96-well plate (the culture solution was 90% DMEM+10% fetal bovine serum), and were incubated in a 37° C., 5% $CO_2$ incubator. 24 hrs later, the compounds were added at different concentrations, and the culture solution was discarded after incubation for 24 hrs. LPS (100 μg/ml)+INF-γ (1 ng/ml) were added. 24 hrs later, the supernatant was collected. The stable metabolic product (nitrite) of NO was used as an index for determining NO, and was determined by Griess Kit.

Results: as shown in FIG. 1, in LPS+INF-γ induced BV2 cells (microglial cells), the production and release of the inflammatory mediator NO were significantly increased. All the compounds of the invention had an inhibitory effect on over-production and release of NO in LPS+INF-γ-induced BV2 cells, indicating that these compounds could significantly antagonize neuroinflammation.

The result showed that the compounds of the invention could be used in the prevention and treatment of a mental disorder such as schizophrenia, and depression, and a nervous system disease such as neurodegenerative disease (e.g. Alzheimer's disease, Parkinson's disease), cerebrovascular disease, brain trauma, spinal cord injury, demyelinating disease, multiple sclerosis, and inflammatory demyelinating polyneuropathy.

EXPERIMENTAL EXAMPLE 2

Effects of the Compounds of the Invention Against Activity of Dopamine D2 Receptor Objective: positive symptoms (hallucination, delusion, etc.) in patients with schizophrenia may be associated with dopamine (DA) hyperfunction in subcortical limbic system, and antipsychotic drugs, which block Dopamine D2 Receptor (DRD2), can effectively control positive symptoms of schizophrenia. By establishing a cell line co-transfected with DRD2 and Gα16, the activated DRD2 can activate Gα16 protein, thereby activating phospholipase C (PLC) to produce inositol 1,4,5-triphosphate ($IP_3$) and diacylglycerol (DAG), wherein $IP_3$ can bind to the $IP_3$ receptor on endoplasmic reticulum and mitochondria, resulting in intracellular calcium release. Therefore, the determination of a change in intracellular calcium can be used as a method for detecting the activated state of DRD2.

Fluo-4/AM was a calcium fluorescent probe indicator for determining calcium ions. In this experiment, a Fluo-4 fluorescence method was used to determine the level of activated Gα protein by measuring the fluorescence intensity excited by intracellular calcium ions. If a compound could activate DRD2, the calcium influx was enhanced; on the contrary, if a compound could antagonize DRD2, the calcium influx was reduced.

Methods: HEK293 cells stably expressing DRD2/Gα16 (a human embryonic kidney cell line, derived from Shanghai Institute of Materia Medica, Chinese Academy of Sciences) were seeded in a 96-well plate (the culture solution was 90% DMEM+10% fetal bovine serum), and incubated overnight. The culture solution was pipetted off, and a freshly prepared dye Fluo-4/AM was added. The cells were incubated in a 37° C. incubator for 40 min. The dye was completely pipetted off. After the cells were washed with a freshly prepared calcium buffer, a calcium buffer (50 μl) dissolved with a test drug was added. FlexStation II instrument was used in the determination. A calcium buffer (25 μl) dissolved with a known agonist was added automatically by the instrument at the fifteenth second, and the fluorescence value at 525 nm (an excitation wavelength of 485 nm) was finally read. Dopamine was used as agonist, Eticlopride (D2 receptor antagonist) was used as antagonist, and the cell response (% Response) of each sample at each concentration was calculated by the following formula: % Response= $(L_{Sample}-L_{Blank})/(L_{Dopamine}-L_{Blank})$, wherein $L_{Sample}$ represents the detected signal value of a test sample, $L_{Blank}$ represents the detected signal value as completely inhibited by Eticlopride, and $L_{Dopamine}$ represents the detected signal value after the stimulation of the DMSO group with 50 nM Dopamine (agonist). $IC_{50}$ value was calculated by GraphPad Prism.

Figure 2:
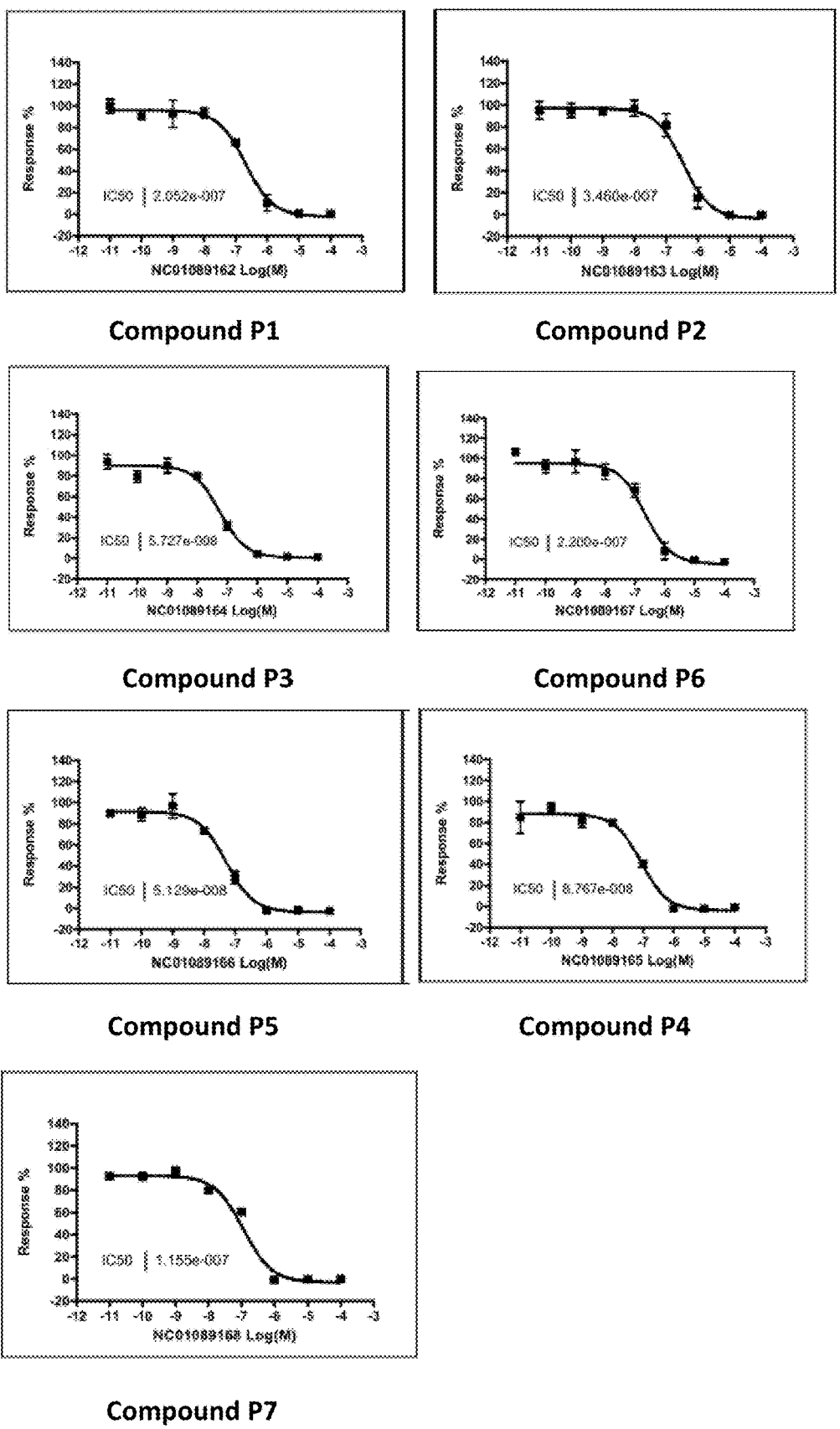
FIG. 2 shows the antagonize activity of the compounds of the invention against dopamine D2 receptor (DRD2).

Results: as seen from Table 1 and FIG. 2, the compounds P1~P7 of the invention could inhibit the activity of dopamine D2 receptor (DRD2) with a certain dosage-effect. The result showed that the compounds of the invention could be used in the prevention and treatment of a mental disorder such as schizophrenia.

TABLE 1

$IC_{50}$ value of a part of compounds of the invention for inhibiting dopamine D2 receptor

| Test compound | $IC_{50}$ (M) | 95% confidence limit (M) |
|---|---|---|
| P1 | $2.052 \times 10^{-7}$ | $1.298 \times 10^{-7}$~$3.244 \times 10^{-7}$ |
| P2 | $3.460 \times 10^{-7}$ | $1.800 \times 10^{-7}$~$6.652 \times 10^{-7}$ |
| P3 | $5.727 \times 10^{-8}$ | $3.590 \times 10^{-8}$~$9.134 \times 10^{-8}$ |
| P6 | $2.200 \times 10^{-7}$ | $1.211 \times 10^{-7}$~$3.995 \times 10^{-7}$ |
| P5 | $5.129 \times 10^{-8}$ | $3.336 \times 10^{-8}$~$7.886 \times 10^{-8}$ |
| P4 | $8.767 \times 10^{-8}$ | $4.919 \times 10^{-8}$~$1.563 \times 10^{-7}$ |
| P7 | $1.155 \times 10^{-7}$ | $6.827 \times 10^{-8}$~$1.954 \times 10^{-7}$ |

EXPERIMENTAL EXAMPLE 3

Effects of the Compounds of the Invention onNMDA Receptor Antagonist-Induced Schizophrenia Mouse Model Objective: Glutamatergic hypofunction is one of the pathogenesis for mental disorders such as schizophrenia. N-methyl-D-aspartic acid (NMDA) receptor antagonists can induce schizophrenia-like effects. In this experiment, a hyperlocomotion schizophrenia model in mice induced by dizocilpine (MK-801), a NMDA receptor antagonist, was used to investigate the in vivo activity of the compounds P6, P5, P4 and P7 of the invention.

Methods: SPF grade inbred Balb/c male mice with no special pathogens (purchased from Laboratory Animal Center of Capital Medical University), weighed (20±2) g, were randomly divided into a control group, a model group, and drug groups. The mice were adapted to the rearing environment for one week, and then were intragastrically administered for 3 days, wherein the control group and model group were intragastrically administered with physiological saline, and on Day 4, the mice were administered prior to test, and then were tested for 60 min in an Open-Field Activity Monitoring System. The control group was then intraperitoneally injected with physiological saline, the model group and the drug groups were intraperitoneally injected with a solution (0.6 mg/kg) of a NMDA receptor antagonist dizocilpine (MK-801), and the mice of these groups were further monitored for spontaneous activity and center square activity within 210 minutes, wherein spontaneous activity was used to reflect the positive symptom of rapid motion in schizophrenia, and center square activity was used to evaluate the anxiety status of schizophrenia.

Figure 3:
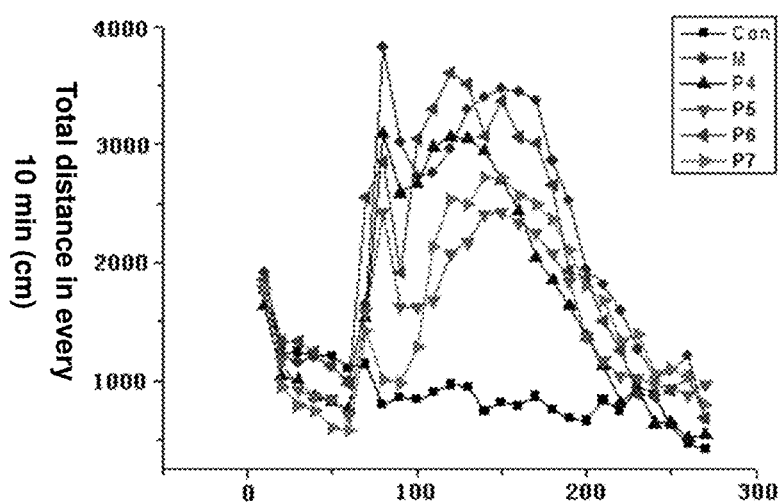
FIG. 3 shows the effects of the compounds of the invention on spontaneous activity in MK-801-induced active schizophrenia model mice within 270 min, wherein the mice were tested for 60 min by an Open-Field Activity Monitoring System, and then, the control group (Con) was intraperitoneally injected with physiological saline, and the model group (M) and the drug groups (P4, P5, P6, P7) were intraperitoneally injected with MK-801; the mice of these groups were continuously monitored for spontaneous activity and center square activity within 210 minutes, and the mice were tested every 10 min, n=10 for each group.
Figure 4:
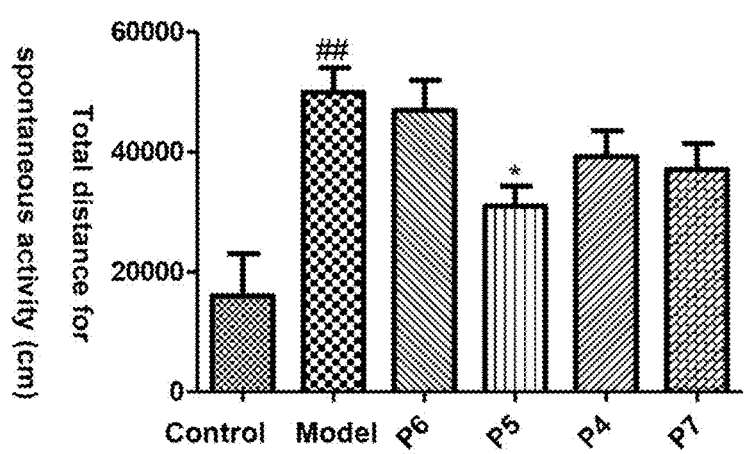
FIG. 4 shows the effects of the compounds of the invention on the total distance for spontaneous activity in MK-801-induced hyperlocomotive schizophrenia model mice within 210 min, wherein the data was expressed as Mean±SE, n=10 for each group; $^{\#\#}P<0.01$, the model group was compared with the control group; $*P<0.05$, the drug group was compared with the Model group.
Figure 5:
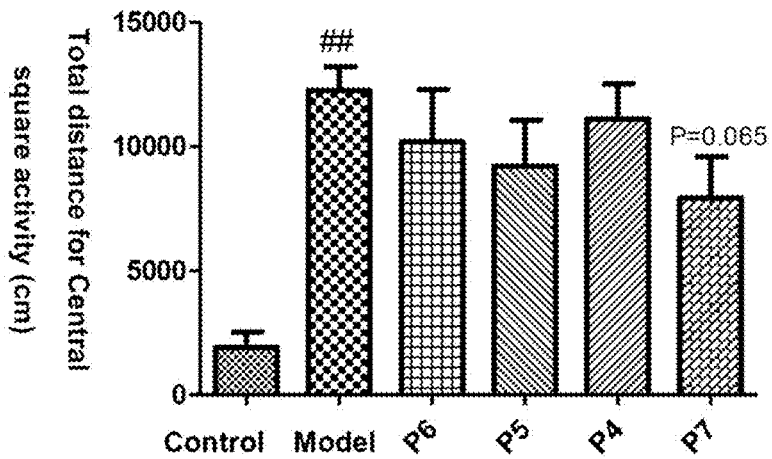
FIG. 5 shows the effects of the compounds of the invention on the total distance for center square activity in MK-801-induced hyperlocomotive schizophrenia model mice within 210 min, wherein the data was expressed as Mean±SE, n=10 for each group; $^{\#\#}P<0.01$, the model group was compared with the control group.

Results: open field test was used to monitor the spontaneous activity of mice, and the result showed that as compared with the control group, the mice in the MK-801 model group had a prolonged total distance of spontaneous activity and a prolonged distance of center square activity within 210 min; intragastrical administration of the compounds P6, P5, and P7 of the invention could shorten the total distance of spontaneous activity and the distance of center square activity (FIG. 3, FIG. 4, FIG. 5, and Table 2). The result showed that the compounds of the invention could alleviate the positive symptoms and anxiety state of schizophrenia.

TABLE 2

Effects of the compounds of the invention on the total distance of spontaneous activity and the distance of center square activity in MK-801-induced hyperlocomotion schizophrenia model in mice within 210 min (open-field test)

| Group | Dose (mg/kg) | Total distance traveled (cm) | Distance of central district activity (cm) |
|---|---|---|---|
| Normal control | — | 15979 ± 2228 | 1903 ± 627 |
| Model | — | 49932 ± 4059[##] | 12248 ± 955[##] |
| Model + P6 | 50 | 46922 ± 2233 | 10181 ± 2110 |
| Model + P5 | 50 | 30914 ± 3351* | 9211 ± 1845 |
| Model + P4 | 50 | 39222 ± 4300 | 11098 ± 1422 |
| Model + P7 | 50 | 37051 ± 4308 | 7913 ± 1666 |

The data was expressed as Mean ± SE, n = 10 for each group;
[##]$P < 0.01$, the model group was compared with the control group;
*$P < 0.05$, the drug group was compared with the model group.

EXPERIMENTAL EXAMPLE 4

Effects of the Compounds of the Invention on Ethological Change in a Cuprizone Model in Mice Objective: neuroinflammation, pathological changes in white matter, and demyelination are the important pathogenesis for many central nervous system diseases. Cuprizone (dicyclohexanoneoxaly dihydrazone) can cause changes such as inflammation, demyelination, axonal injury, and cognitive function impairment. In this experiment, Y-maze and open-field behavior test were used to study the effects of the compounds of the invention on memory function and motion in a Cuprizone mouse model.

Methods: SPF grade inbred C57BL/6 male mice, weighed (20±2) g, were randomly divided into a control group, a model group, and drug groups. The mice were adapted to the rearing environment for 3 days. Then, the control group was fed with a normal feed, and the other groups were fed with a feed containing 0.2% Cuprizone for model establishment. During model establishment, the mice in each group were intragastrically administered with a corresponding dose of drug, and were reared for 5 weeks. The mice were then subjected to the Y-maze and open field behavior test, wherein the number of arm entries in Y-maze was used to reflect the motion of mice; the spontaneous alternation in Y maze was used to reflect the working memory of mice; and the spontaneous activity in open-field behavior test was used to reflect the motion of mice.

Figure 6:
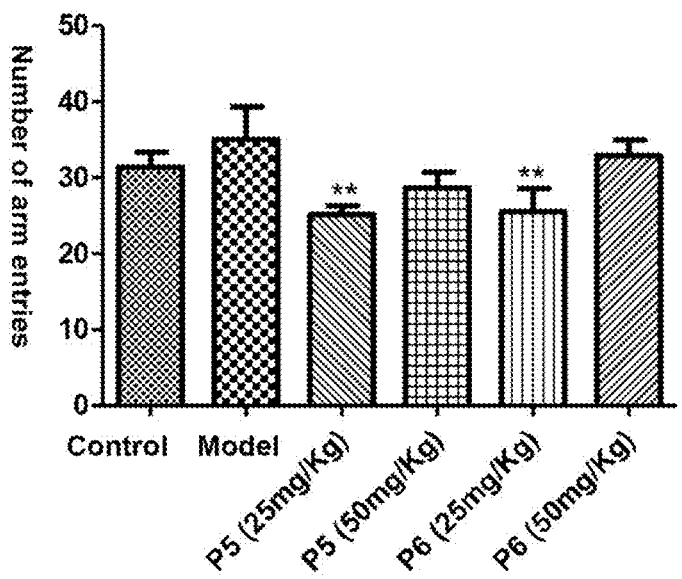
FIG. 6 shows the effect of the compounds of the invention on the number of arm entries in Cuprizone model mice in Y-maze within 8 min, wherein the data was expressed as Mean±SE, n=8 for each group, *P<0.05; **P<0.01; the drug group was compared with the Model group.
Figure 7:
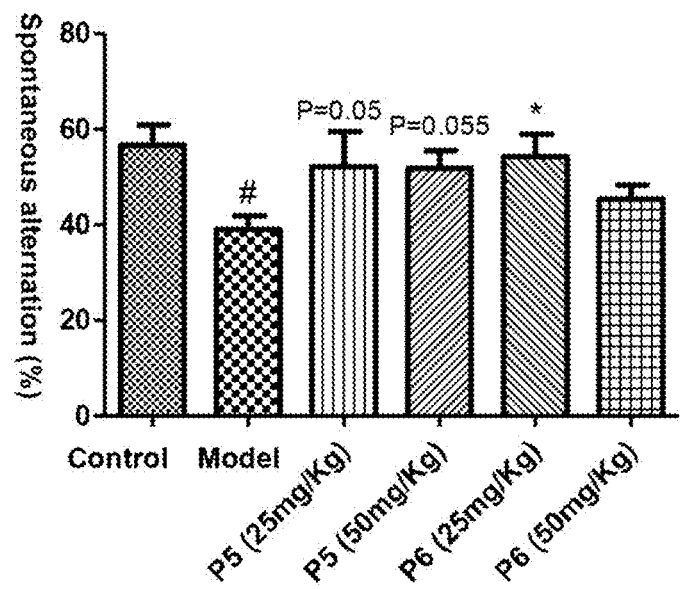
FIG. 7 shows the effects of the compounds of the invention on spontaneous alternation in Cuprizone model mice in Y-maze within 8 min, wherein the data was expressed as Mean±SE, n=8 for each group, #P<0.05, the model group was compared with the control group; *P<0.05, the drug group of the invention was compared with the Model group.
Figure 8:
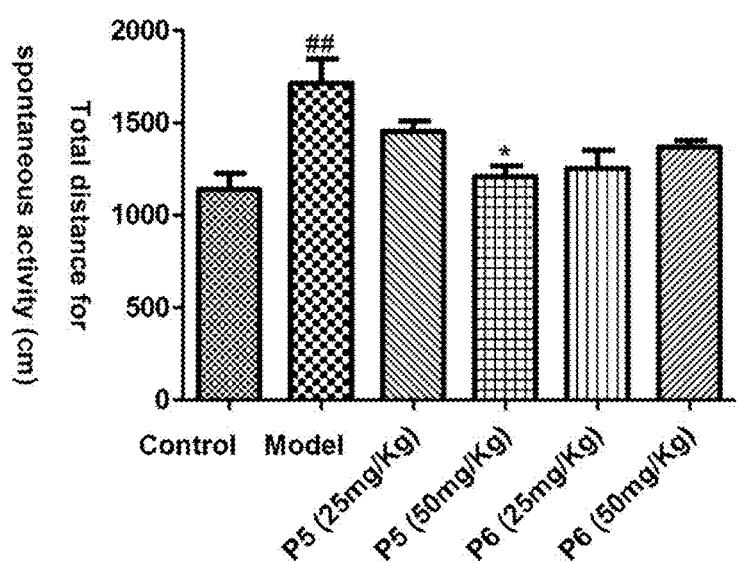
FIG. 8 shows the effects of the compounds of the invention on total distance for spontaneous activity in Cuprizone model mice within 10 min, wherein the data was expressed as Mean±SE, n=8 for each group, ##P<0.01, the model group was compared with the control group; *P<0.05, the drug group of the invention was compared with the Model group.

Results: the result of Y-maze test showed that as compared with the control group, Cuprizone model mice had an increase in the number of arm entries, and a reduction in the spontaneous alternation; the intragastrical administration of the compounds P6 and P5 of the invention could reduce the number of arm entries (FIG. 6), and enhance the spontaneous alternation (FIG. 7) in the model mice. The result of open-field test showed that as compared with the control group, Cuprizone model mice had a longer total distance of spontaneous activity; the intragastrical administration of the compounds P6 and P5 of the invention could shorten the total distance of spontaneous activity in the model mice (FIG. 8). The result showed that the compounds of the invention could improve the cognitive function and motor behavior in Cuprizone model mice, and alleviate the high activity in model mice.

EXPERIMENTAL EXAMPLE 5

Effect of the Compounds of the Invention on Demyelination in a Cuprizone Mouse Model Objectiv: pathological changes in white matter and demyelination are the important pathogenesis for many central nervous system diseases and mental disorders. Cuprizone can cause demyelination and pathological changes in white matter. Myelin basic protein (MBP) is a marker protein for myelination of axons, and is the main component of myelin sheath. In this experiment, Western Blot method was used to study the effects of the compounds of the invention on the MBP content and demyelination in the brain of Cuprizone model mice.

Methods: Cuprizone mouse model establishment and administration method were the same as those described in Experimental example 4. After ethological tests were performed, the mice were anaesthetized by intraperitoneal injection of 10% chloral hydrate. The brains were harvested and stored at −80° C. Western blot assay: brain tissue was lysed with lysate to extract protein, and the protein concentration was determined. SDS-PAGE gel electrophoresis was performed, the protein was transferred onto a membrane, and the membrane was blocked. The protein was incubated with an anti-MBP antibody (a primary antibody) overnight at 4° C. in a refrigerator. After rinsing with TBST, it was incubated with a goat anti-mouse IgG antibody (a secondary antibody) at 4° C. in a refrigerator for 2 hrs. After washing the membrane with TBST, an ECL solution was added in a dark room, followed by tabletting, and exposure. Signal intensity for each protein band was analyzed using FluorChem 8900 gray-scale analysis software.

Figure 9:
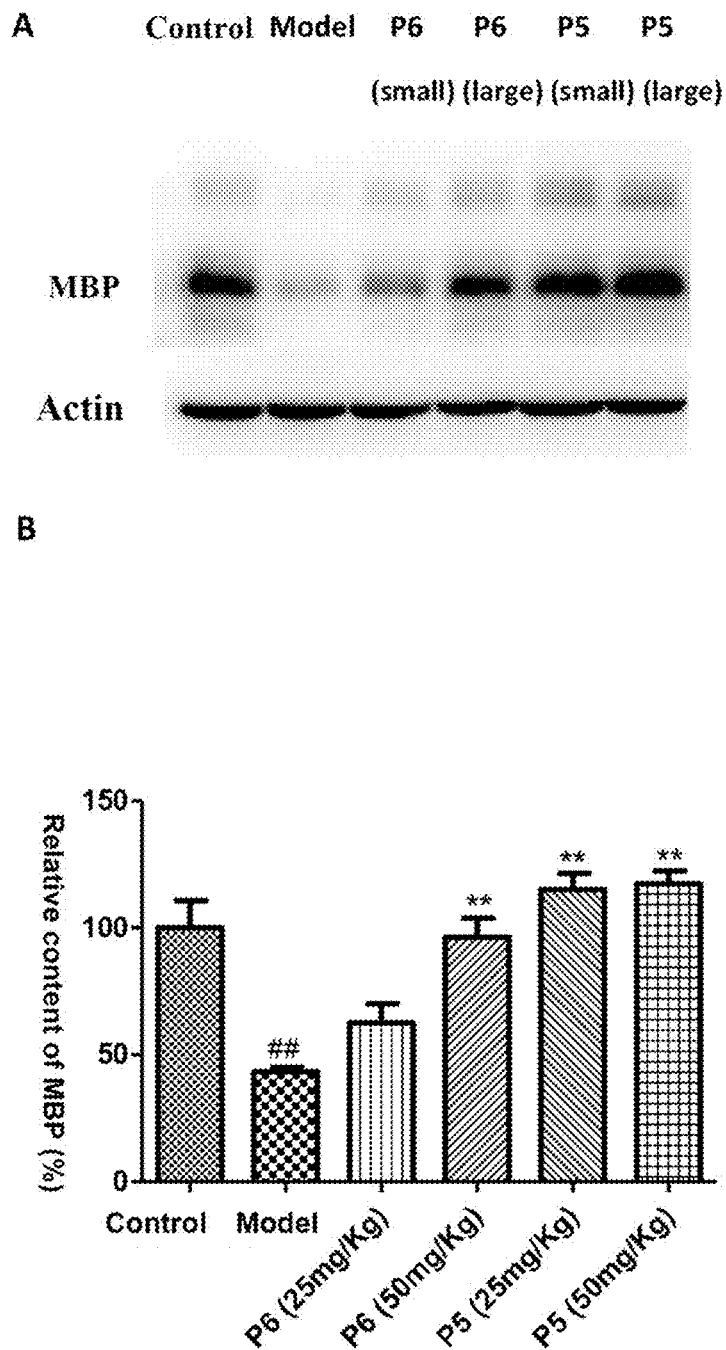
FIG. 9 shows the effect of the compounds of the invention on myelin basic protein (MBP) in the frontal contex of Cuprizone model mice, wherein (A) is a representative Western blot photo of MBP protein, S: small-dose group, 25 mg/kg; L: large-dose group, 50 mg/kg; and (B) is the quantitative result of MBP protein, wherein the data was expressed as Mean±SE, n=4, ##P<0.01, as compared with the control group; **P<0.01, as compared with the Model group.

Result: in the Western blot assay, the result showed that: as compared with the control group, the mice in the Cuprizone model group had the MBP content decreased significantly in frontal cortex; the compounds P5 and P4 of the invention could significantly enhance the MBP content in model mice, indicating that they could improve demyelination (FIG. 9).

The result showed that the compounds of the invention could be used in the prevention and treatment of schizophrenia, depression and other mental disorders, as well as diseases such as cerebrovascular disease, demyelinating disease, multiple sclerosis, inflammatory demyelinating polyneuropathy, ischemic leukoencephalopathy, hypoxic leukoencephalopathy, and diabetic neuropathy.

EXPERIMENTAL EXAMPLE 6

Effects of the Compounds of the Invention on Microglial Cell Activation in a Cuprizone Mouse Model Objective: microglial activation and neuroinflammation are the important pathogenesis for many central nervous system diseases. Iba-1 could specifically label microglial cells. In this experiment, immunohistochemical method was used to study the effects of the compounds of the invention on Iba-1-labeled microglial cells in the brain of Cuprizone model mice.

Methods: Cuprizone mouse model establishment and administration method were the same as those described in Experimental example 4. After ethological tests were performed, the mice were anaesthetized by intraperitoneal injection of 10% chloral hydrate. After perfusion, brain tissue was taken and fixed with 15% paraformaldehyde, and then frozen and sliced. Immunohistochemical staining: the frozen sections were inactivated with 3% $H_2O_2$ for 10 min and rinsed with PBS; the tissues were blocked with 10% serum and incubated at 37° C. for 1 h. Serum was washed off and a primary antibody (an anti-Iba-1 antibody) was added dropwise. The resultant mixture was kept at 4° C. overnight. After rinsing with PBST, a biotin-conjugated goat anti-rabbit IgG antibody (a secondary antibody) was added dropwise, and incubated at 37° C. for 2 hrs. After rinsing with PBST, a horseradish peroxidase-conjugated streptavidin (a third antibody) was added dropwise, and incubated at 37° C. for 2 hrs. After rinsing with PBS, DAB reagent was used to develop color, and the stained cells were transparent, and were mounted. Iba-1 positive cells were observed under microscope, and counted.

Figure 10:
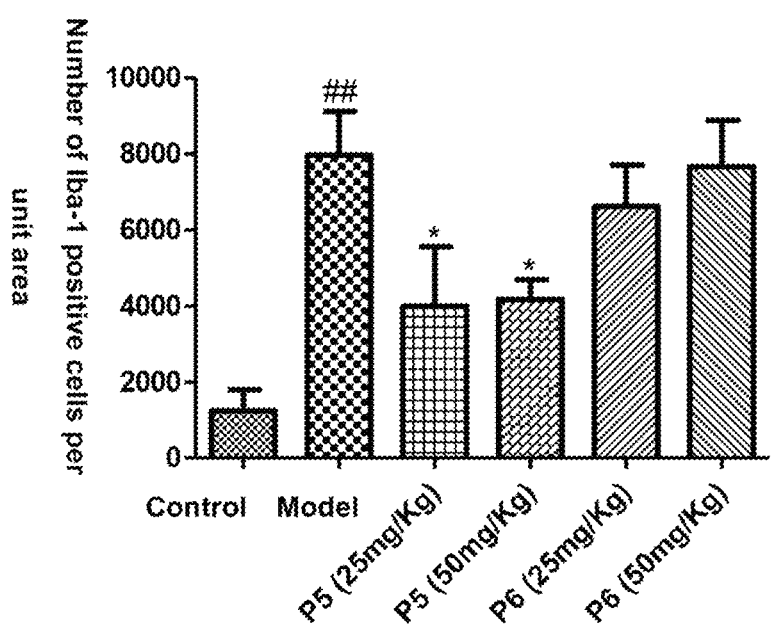
FIG. 10 shows the effect of the compounds of the invention on microglial cells in the brain of Cuprizone model mice (immunohistochemical staining), wherein the data was expressed as Mean±SE, n=3, ##P<0.01, as compared with the control group; *P<0.05, as compared with the Model group.

Results: immunohistochemical staining result showed that as compared with the normal control group, the number of Iba-1-labeled microglial cells increased significantly in the brain of the Cuprizone model group, indicating that microglial cells were activated, and inflammation occurred; the compound P6 (25, 50 mg/kg) of the invention could significantly reduce the number of microglial cells, indicating that it could inhibit microglial cell activation, and alleviate inflammation (FIG. 10).

The result showed that the compounds of the invention can be used in the prevention and treatment of a mental disorder such as schizophrenia and depression, and a nervous system disease such as neurodegenerative disease (e.g. Alzheimer's disease, Parkinson's disease), cerebrovascular disease, brain trauma, spinal cord injury, demyelinating disease, multiple sclerosis, or inflammatory demyelinating polyneuropathy.

To sum up, the invention provides a class of novel compounds of Formula I, which can antagonize dopamine D2 receptor, and inhibit microglial activation and neuroinflammation; the animal experimental results showed that the compounds of the invention can reduce the hyperlocomotion in MK-801 model mice, and alleviate anxiety status; can improve memory dysfunction, abnormal motor behavior and hyperlocomotion in Cuprizone model mice, and inhibit microglial cell activation and demyelination in the model mice. These results showed that the compounds of the invention can be used in the prevention and treatment of various mental disorders and nervous system diseases.

Although the embodiments of the invention have been described in detail, a person skilled in the art would understand that a variety of modifications and replacements, which are performed to the details according to all the disclosed teachings, all fall into the protection scope of the invention. The scope of the invention is defined by the attached claims and any equivalent thereof.

The invention claimed is:
1. A compound of Formula (I) or a pharmaceutically acceptable salt thereof:

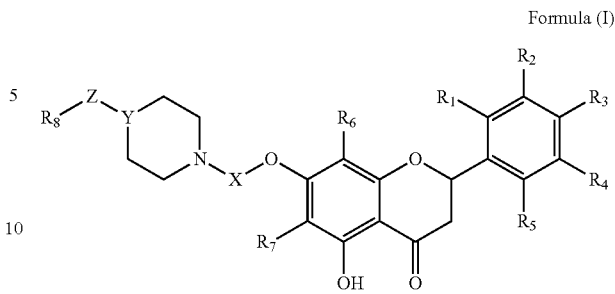

Formula (I)

wherein:
$R_1$, $R_2$, $R_3$, $R_4$, $R_5$, $R_6$, $R_7$ and $R_8$ are independently selected from the group consisting of hydrogen, halogen, cyano, hydroxyl, amino, $C_{1-6}$alkyl, $C_{1-6}$alkoxy, $C_{1-6}$alkylamino and aryl, optionally, wherein the $C_{1-6}$alkyl, $C_{1-6}$alkoxy, $C_{1-6}$alkylamino and aryl are independently substituted with one or more substituents selected from the group consisting of halogen, amino and hydroxyl;

X is a saturated or partially saturated alkylene containing 2-6 carbon atoms, optionally, wherein the alkylene is substituted by hydroxyl or methyl;

Y is N or C(R), wherein R is selected from the group consisting of hydrogen, hydroxyl, amino, and $C_{1-6}$alkyl; and Z is aryl or heteroaryl.

2. The compound or the pharmaceutically acceptable salt thereof according to claim 1, wherein $R_1$, $R_2$, $R_4$, $R_5$, $R_6$ and $R_7$ are independently selected from the group consisting of hydrogen, halogen, cyano, hydroxyl, amino, $C_{1-6}$alkyl, $C_{1-6}$alkoxy, $C_{1-6}$alkylamino and 6-20-membered aryl.

3. The compound or the pharmaceutically acceptable salt thereof according to claim 1, wherein $R_3$ is selected from the group consisting of hydrogen, halogen, $C_{1-6}$alkyl and $C_{1-6}$alkoxy, optionally, wherein the $C_{1-6}$alkyl and $C_{1-6}$alkoxy are independently substituted with one or more substituents selected from the group consisting of halogen, amino and hydroxyl.

4. The compound or the pharmaceutically acceptable salt thereof according to claim 1, wherein $R_8$ is selected from the group consisting of hydrogen, halogen, $C_{1-6}$alkyl and $C_{1-6}$alkoxy, optionally, wherein the $C_{1-6}$alkyl and $C_{1-6}$alkoxy are independently substituted with one or more substituents selected from the group consisting of halogen, amino and hydroxyl.

5. The compound or the pharmaceutically acceptable salt thereof according to claim 1, wherein Y is N or C(R), and R is selected from the group consisting of hydrogen, hydroxyl and methyl.

6. The compound or the pharmaceutically acceptable salt thereof according to claim 1, wherein X is $C_{2-6}$alkylene, optionally, wherein the $C_{2-6}$alkylene is substituted by hydroxyl or methyl.

7. The compound or the pharmaceutically acceptable salt thereof according to claim 1, wherein Z is aryl or heteroaryl containing 5-20 carbon atoms,
optionally, wherein the aryl or heteroaryl is selected from the group consisting of phenyl, naphthyl, pyrrolyl, furyl, thienyl, imidazolyl, pyrazolyl, oxazolyi, isoxazolyl, thiazolyl, isothiazolyl, triazolyl, pyridyl, pyranyl, pyrimidinyl, pyrazinyl, pyridazinyl, triazinyl, indolyl, benzofuryl, benzothienyl, benzoimidazolyl, benzopyrazolyl, benzoxazolyl, benzisoxazolyl, benzothiazolyl, benzoisothiazolyl, benzotriazolyl, quinolyl, benzopyranyl, benzopyrimidinyl, quinoxalinyl, benzopyridazinyl, benzotriazinyl and purinyl.

8. The compound or the pharmaceutically acceptable salt thereof according to claim 1, wherein the compound is selected from the group consisting of:

5-hydroxy-2-(4-methoxyphenyl)-7-(4-(4-(2-methoxyphenyl)-piperazin-1-yl)-butoxy)-chroman-4-one;

5-hydroxy-2-(4-methylphenyl)-7-(4-(4-(2-methoxyphenyl)-piperazin-1-yl)-butoxy)-chroman-4-one;

5-hydroxy-2-(4-fluorophenyl)-7-(4-(4-(2-methoxyphenyl)-piperazin-1-yl)-butoxy)-chroman-4-one;

5-hydroxy-2-methoxyphenyl)-7-(4-(4-(2-methoxyphenyl)-piperazin-1-yl)-propoxy)-chroman-4-one;

5-hydroxy-2-methoxyphenyl)-7-(4-(4-(6-fluoro-benzo[d]isoxazol-3-yl)-piperidin-1-yl)-butoxy)-chroman-4-one;

5-hydroxy-2-methoxyphenyl)-7-(4-(4-(6-fluoro-benzo[d]isoxazol-3-yl)-piperidin-1-yl)-propoxy)-chroman-4-one; and 5-hydroxy-2-fluorophenyl)-7-(4-(4-(6-fluoro-benzo[d]isoxazol-3-yl)-piperidin-1-yl)-butoxy)-chroman-4-one.

9. A pharmaceutical composition, comprising the compound or the pharmaceutically acceptable salt thereof according to claim 1, and optionally one or more pharmaceutically acceptable adjuvants.

10. A method for preparing the compound or the pharmaceutically acceptable salt thereof according to claim 1, comprising the following steps of:

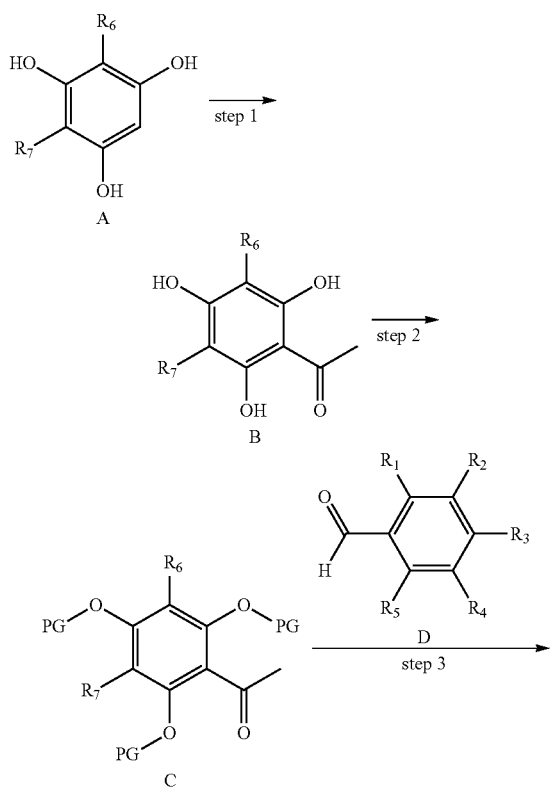

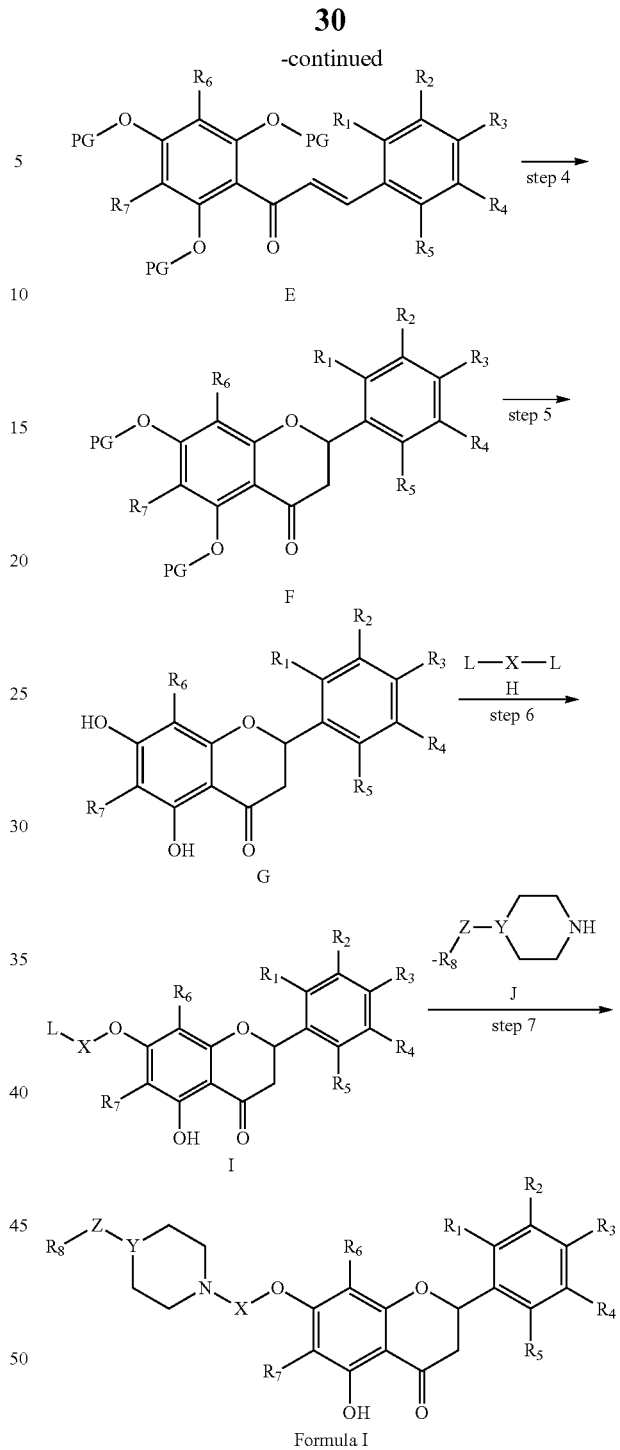

1) Compound A and acetyl chloride are subjected to acylation reaction to produce Compound B;
2) Protective groups for the hydroxyl groups of Compound B are introduced to produce Compound C;
3) Compound C and Compound D are subjected to aldol condensation reaction to produce Compound E;
4) Compound E is subjected to ring-closure reaction to produce Compound F;
5) Compound F is deprotected to produce Compound G;
6) Compound G and Compound H are subjected to nucleophilic substitution to produce Compound I; and,
7) Compound I and Compound J are subjected to nucleophilic substitution to produce Compound of Formula I;

wherein, PG represents a hydroxyl protecting group; L represents a leaving group of the nucleophilic substitution reaction;

the other atoms or substituents have the same meanings as defined in claim 1.

11. A method for treating a mental disorder or a nervous system disease, comprising administering to a subject in need thereof an effective amount of the compound or the pharmaceutically acceptable salt thereof according to claim 1 or a pharmaceutical composition comprising the compound or the pharmaceutically acceptable salt thereof and optionally one or more pharmaceutically acceptable adjuvants;

wherein, the mental disorder is selected from the group consisting of schizophrenia, depression, manic depressive disorder, cognitive disorder, anxiety disorder, stress related disorder, attention deficit hyperactivity disorder, tic disorder, and mental disorder associated with organic lesion; the nervous system disease is selected from the group consisting of neurodegenerative disease, Alzheimer's disease, Parkinson's disease, cerebrovascular disease, brain trauma, spinal cord injury, demyelinating disease, multiple sclerosis, inflammatory demyelinating polyneuropathy, ischemic leukoencephalopathy, hypoxic leukoencephalopathy and diabetic neuropathy.

12. A method for
(1) inhibiting over activation or proliferation of microglial cells,
(2) inhibiting the activity of dopamine receptor in a cell,
(3) enhancing the activity of NMDA receptor in a cell, or
(4) enhancing the content of myelin basic protein (MBP) in a cell, or reducing demyelination or pathological changes in white matter, comprising administering to the cell(s) an effective amount of the compound of Formula I or the pharmaceutically acceptable salt thereof according to claim 1 or a pharmaceutical composition comprising the compound or the pharmaceutically acceptable salt thereof and optionally one or more pharmaceutically acceptable adjuvants.

13. The compound or the pharmaceutically acceptable salt thereof according to claim 1, wherein $R_1$, $R_2$, $R_4$, $R_5$, $R_6$ and $R_7$ are independently selected from the group consisting of hydrogen, halogen, cyano, hydroxyl, amino and $C_{1-4}$alkyl.

14. The compound or the pharmaceutically acceptable salt thereof according to claim 1, wherein $R_1$, $R_2$, $R_4$, $R_5$, $R_6$ and $R_7$ are hydrogen.

15. The compound or the pharmaceutically acceptable salt thereof according to claim 1, wherein $R_3$ is selected from the group consisting of hydrogen, halogen, $C_{1-4}$alkyl and $C_{1-4}$alkoxy, optionally, wherein the $C_{1-4}$alkyl and $C_{1-4}$alkoxy are independently substituted with one or more substituents selected from the group consisting of halogen, amino and hydroxyl.

16. The compound or the pharmaceutically acceptable salt thereof according to claim 1, wherein $R_3$ is selected from the group consisting of hydrogen, halogen, $C_{1-2}$alkyl and $C_{1-2}$alkoxy.

17. The compound or the pharmaceutically acceptable salt thereof according to claim 1, wherein $R_3$ is selected from the group consisting of fluorine, methyl and methoxy.

18. The compound or the pharmaceutically acceptable salt thereof according to claim 1, wherein $R_8$ is selected from the group consisting of hydrogen, halogen, $C_{1-2}$alkyl and $C_{1-2}$alkoxy.

19. The compound or the pharmaceutically acceptable salt thereof according to claim 1, wherein $R_8$ is selected from the group consisting of fluorine and methoxy.

20. The compound or the pharmaceutically acceptable salt thereof according to claim 1, wherein Y is N or CH.

21. The compound or the pharmaceutically acceptable salt thereof according to claim 1, wherein X is 1,3-propylene or 1,4-butylene.

22. The method according to claim 11, wherein the mental disorder associated with organic lesion is selected from the group consisting of Alzheimer's disease, vascular dementia, mental disorder caused by brain trauma, mental disorder caused by intracranial infection, mental disorder caused by brain tumor, mental disorder caused by syphilis, epileptic mental disorder, mental disorder caused by HIV/AIDS.

* * * * *